(12) United States Patent
Vlodavsky et al.

(10) Patent No.: US 7,772,187 B2
(45) Date of Patent: Aug. 10, 2010

(54) SUBSTANCES DIRECTED AGAINST A SPECIFIC SEQUENCE ESSENTIAL FOR HEPARANASE CATALYTIC ACTIVITY AND USES THEREOF AS HEPARANASE INHIBITORS

(75) Inventors: Israel Vlodavsky, Mevasseret Zion (IL); Neta Ilan, Rehovot (IL); Flonia Levy-Adam, Haifa (IL)

(73) Assignees: Hadasit Medical Research Services and Development Company, Ltd., Jerusalem (IL); Rappaport Family Institute for Research in the Medical Sciences, Haifa (IL)

(*) Notice: Subject to any disclaimer, the term of this patent is extended or adjusted under 35 U.S.C. 154(b) by 411 days.

(21) Appl. No.: 10/901,943

(22) Filed: Jul. 28, 2004

(65) Prior Publication Data

US 2005/0169907 A1 Aug. 4, 2005

(30) Foreign Application Priority Data

Jan. 22, 2004 (IL) ...................................... 160025

(51) Int. Cl.
  *A61K 38/10* (2006.01)
  *C12N 9/24* (2006.01)
  *C07K 7/08* (2006.01)
(52) U.S. Cl. .......................... 514/14; 435/200; 514/13; 530/326; 530/327
(58) Field of Classification Search ........................ None
  See application file for complete search history.

(56) References Cited

U.S. PATENT DOCUMENTS

| 6,387,643 B1 | 5/2002 | Heinrikson et al. |
| 2002/0068061 A1 | 6/2002 | Peretz et al. |
| 2007/0253970 A1* | 11/2007 | Schirrmacher et al. ... 424/185.1 |

FOREIGN PATENT DOCUMENTS

WO  WO 99/43830  9/1999

OTHER PUBLICATIONS

GenBank Accession No. AAD41342 heparanse, *Homo sapiens*, Jun. 29, 1999.*
GenBank Accession No. NP_072127, heparanase, *Rattus norvegicus*, Mar. 11, 2007, the earliest priority date 2002.*
Sigma Catalog, p. 620 (1993).*
Laura E. Benjamin and Eli Keshet, Conditional switching of vascular endothelial growth factor (VEGF) expression in tumors: Induction of endothelial cell shedding and regression of hemangioblastoma-like vessels by VEGF withdrawal, Proc. Natl. Acad. Sci., Aug. 1997, p. 8761-8766, vol. 94.
Dominique Bernard, Bruo Mehul, Caroline Delattre, Lucie Simonetti, Agnes Thomas-Collignon, and Rainer Schmidt, Purification and Characterization of the Endoglycosidase Heparanase 1 from Human Plantar Stratum Corneum: a Key Enzyme in Epidermal Physiology?, J. Invest. Derm., Nov. 2001, p. 1266-1273, vol. 117, No. 5.
Julie H. Campbell, Robyn E. Rennick, Silvia G. Kalevitch, and Gordon R. Campbell, Heparan Sulfate-Degrading Enzymes Induce Modulation of Smooth Muscle Phenotype, Experimental Cell Research 200, 1992, p. 156-167.
Laurie A. Dempsey, Timothy B. Plummer, Sarah L. Coombes and Jeffrey L. Platt, Heparanase expression in invasive trophoblast and acute vascular damage, Glycobiology, 2000, p. 467-475, vol. 10 No. 5.
Laurie A. Dempsey, Gregory J. Brunn and Jeffrey L. Platt, Heparanase, a potential regulator of cell-matrix interactions, Tibs 25, Aug. 2000, p. 349-351.
Stefan Drose and Karlheinz Altendorf, Bafilomycins and concanamycins as inhibitors of V-ATPases and P-ATPases, The Journal of Experimental Biology 200, 1997, p. 1-8.
Morten Egeberg, Rune Kjeken, Svein O. Kolset, Trond Berg, Kristian Prydz, Internalization and stepwise degradation of heparanase sulfate proteoglycans in rat hepatocytes, Biochimica et Biophysics Acta 1541, 2001, p. 135-149.
Osama N. El-Assal, Akira Yamanoi, Takashi Ono, Hitoshi Kohno, and Naofumi Nagasue, The Clinicopathological Significance of Heparanase and Basic Fibroblast Growth Factor Expressions in Hepatocellular Carcinoma, Clinical Cancer Research, May 2001, p. 1299-1305, vol. 7.
Michael Elkin, Irit Cohen, Eyal Zcharia, Adam Orgel, Zehava Guatta-Rangini, Tamar Peretz, Israel Vlodavsky, and Hynda K. Kleinman, Regulation of Heparanase Gene Expression by Estrogen in Breast Cancer, Cancer Research 63, Dec. 15, 2003, p. 8821-8826.
Michael B. Fairbanks, Ana M. Mildner, Joseph W. Leone, Gregory S. Cavey, W. Rodney Mathews, Roger F. Drongs, Jerry L. Slightom, Michael J. Bienkowski, Clark W. Smith, Carol A. Bannow, and Robert L. Heinrikson, Processing of the Human Heparanase Precursor and Evidence That the Active Enzyme Is a Heterodimer, The Journal of Biological Chemistry, Oct. 15, 1999, p. 29587-29590, vol. 274 No. 42.
Craig Freeman, and Christopher R. Parish, A rapid quantitative assay for the detection of mammalian heparanase activity, Biochem. J., 1997, p. 229-237.

(Continued)

*Primary Examiner*—Rebecca Prouty
(74) *Attorney, Agent, or Firm*—Martin Fleit; Paul D. Bianco; Fleit Gibbons Gutman Bongono & Bianco PL

(57) ABSTRACT

An amino acid sequence derived from the N' terminus region of the 50 Kd subunit of heparanase, preferably, the sequence including amino acid residues $Lys^{158}$-$Asn^{171}$ of human heparanase and any functional fragments thereof. Compositions for the inhibition of heparanase glycosidase catalytic activity, having as an active ingredient an isolated and purified peptide as the amino acid sequence. An antibody directed to the sequence and compositions and uses thereof as heparanase inhibitor. The use of the amino acid sequence in a screening method for specific heparanase inhibitors. Compositions including the heparanase inhibitors and methods for the treatment of heparanase related disorders.

37 Claims, 7 Drawing Sheets

OTHER PUBLICATIONS

Svetlana Gingis-Velitski, Anna Zetser, Victoria Kaplan, Olga Ben-Zaken, Esti Cohen, Flonia Levy-Adam, Yulia Bashenko, Moshe Y. Flugelman, Israel Vlodavsky, and Neta Ilan, Heparanase Uptake Is Mediated by Cell Membrane Heparan Sulfate Proteoglycans,The Journal of Biological Chemistry, Oct. 15, 2004, p. 44084-44092, vol. 279, No. 42.

Kazuo Gohji, Hiroshi Hirano, Masayuki Okamoto, Sohei Kitazawa, Minako Toyoshima, Jian Dong, Yoji Katsuoka and Motowo Nakajima, Expression of three extracellular matrix degradative enzymes in bladder cancer, Int. J. Cancer, 2001, p. 295-301, vol. 95.

Orit Goldschmidt, Liat Nadav, Helena Aingorn, Cohen Irit, Naomi Feinstein, Neta Ilan, Eli Zamir, Benjamin Geiger, Israel Vlodavsky, and Ben-Zion Katz, Human Heparanase is localized within Lysosomes in a Stable Form, Experimental Cell Research 281, 2002, p. 50-62.

Orit Goldschmidt, Eyal Zcharia, Helena Aingorn, Zehava Guatta-Rangini, Ruth Atzmon, Israel Michael, Iris Peckerr, Eduardo Mitrani, and Israel Vlodavsky, Expression Pattern and Secretion of Human and Chicken Heparanase Are Determined by Their Signal Peptide Sequence,The Journal of Biological Chemistry, 2001, p. 29178-29187, vol. 276, No. 31.

Orit Goldschmidt, Eyal Zcharia, Rinat Abramovitch, Shula Metzger, Helena Aingorn, Yael Friedmann, Volker Schirrmacher, Eduardo Mitrani, and Israel Vlodavsky, Cell surface expression and secretion of heparanase markedly promote tumor angiogenesis and metastasis, Proc. Natl. Acad. Sci., 2002, p. 10031-10036, vol. 99, No. 15.

Ronit Haimov-Kochman, Yael Friedmann, Diana Prus, Debra S. Goldman-Wohl, Caryn Greenfield, Eyal Y. Anteby, Ayelet Aviv, Israel Vlodavsky and Simcha Yagel, Localization of heparanase in normal and pathological human placenta, Molecular Human Reproduction, 2002, p. 566-573, vol. 8, No. 6.

Richard Hoffman, Dietrich H. Paper, Jane Donaldson, Susanne Alban and Gerhard Franz, Characterization of a laminarin sulphate which inhibits basic fibroblast growth factor binding and endothelial cell proliferation, Journal of Cell Science, 1995, p. 3591-3598, vol. 39.

Mark D. Hulett, June R. Hornby, Stephe J. Ohms, Johannes Zuegg, Craig Freeman, Jill E. Gready, and Christopher R. Parish, Identification of Active-Site Residues of the Pro-Metastatic Endoglycosidase Heparanase, Biochemistry, 2000, p. 15659-15667, vol. 39.

Neta Ilan, Itamar Carash, Moshe Raikhinstein, Alexander Faerman, and Moshe Shami, β-Lactoglobulin/Human Serum Albumin Fusion Genes Do Not Respond Accurately to Signals from the Extracellular Matrix in Mammary Epithelial Cells from Transgenic Mice, Experimental Cell Research, 1996, p. 146-159, vol. 228.

Hua-Quan Miao, Michael Elkin, Elena Aingorn, Rivka Ishai-Michaeli, Cy A. Stein, and Israel Vladovsky, Inhibition of Heparanase Actrivity and Tumor Metastasis by Laminarin Sulfate and Synthetic Phosphorothioate, Oligodexynucleotides, Int. J. Cancer, Jun. 8, 1999, p. 424-431, vol. 83.

Liat Nadav, Amiram Eldor, Oron Yacoby-Zeevi, Eli Zamir, Iris Pecker, Neta Ilan, Benjamin Geiger, Israel Vlodavsky, and Den-Zion Kayz, Activation, processing and trafficking of extracellular heparanase by primary human fibroblast, Journal of Cell Science, Dec. 12, 2001, p. 2179-2187, vol. 115.

Rita Nahta, Gabriel N. Hortobagyl, Francisco J. Esteva, Growth Factor Receptors in Breast Cancer: Potential for Therapeutic Intervention, The Oncologist, 2003, p. 5-17, vol. 8.

Motowo Nakajima, Anne Dechavigny, Clarence E. Johnson, Jun-Ichi Hamadat, Cy A. Stein, and Garth L. Nicolson, A Potential Inhibitor of Melanoma Heparanase and Invasion, The Journal of Biological Chemistry, May 25, 1991, p. 9661-9666, vol. 266.

Christopher R. Parish, Craig Freeman and Mark D. Hulett, Heparanase: a key enzyme involved in cell invasion, Biochemica et Biophysica Acta 1471, Jan. 2, 2001, p. M99-M108.

Christopher R. Parish. Craig Freeman, Kathryn J. Brwon, Douglas J. Francis, and William B. Cowden, Identification of Sulfated Oligosaccharide-based inhibitors of Tumor Growth and Metastasis Using Novel in Vitro Assays for Angiogenesis and Heparanase Activity, Cancer Research 59, Jul. 15, 1999, p. 3433-3441.

Christoph Rader, David A. Cheresh, and Carlos F. Barbas III, A phage display approach for rapid antibody humanizarion: Designed combinatorial V gene libraries, Proc. Natl. Acad. Sci., Jul. 1998, p. 8910-8915, vol. 95.

J. Rohloff, J. Zinke, K. Schoppmeyer, A. Tannapfel, H. Witzigmann, J. Mossner, C. Wittekind, and K. Caca, Heparanase expression is a prognostic indicator for postoperative survival in pancreatic adenocarcinoma, British Journal of Cancer, Feb. 11, 2002, p. 1270-1275, vol. 86.

Pesach J. Shteper, Eyal Zcharia, Yaqoub Ashhab, Tamar Peretz, Israel Vlodavsky, and Dina Ben-Yehuda, Role of promoter methylation in regulation of the mammalian heparanase gene, Oncogene 22, 2003, p. 7737-7749.

I. Vlodavsky, A. Eldor, A. Haimovitz-Friedman, Y. Matzner, R. Ishai-Michaeli, O. Lider, Y. Naparstek, I.R. Cohen, Z. Fuks, Expression of Heparanase by Platelets and Circulating Cells of the Immune System: Possible Involvement in Diapedesis and Extravasation, Invasion Metastasis 12, 1992, p. 112-127.

Israel Vlodavsky and Yael Friedmann, Molecular properties and involvement of heparanase in cancer metastasis and angiogenesus, J. Clin. Invest. 108, 2001, p. 341-347.

I. Vlodavsky, M. Mohsen, O. Lider, C.M. Svahn, H.P. Ekre, M. Vigoda, R. Ishai-Michael, T. Peretz, Inhibitor of Tumor Metastasis by Heparanase Inhibiting Species of Heparin, Invasion Metastasis,1994-95, p. 290-302, vol. 14.

Israel Vlodavsky, Yael Friedmann, Michael Elkin, Helena Aingorn Ruth Atzmon, Rivka Ishai-Michaeli, Menachem Bitan, Orit Pappo, Tuvia Peretz, Israel Michal, Larissa Spector and Iris Pecker, Mammalian heparanase: Gene cloning, expression and function in tumor progression and metastasis, Nature Medicine, Jul. 1999, p. 793-802, vol. 5.

Israel Vlodavsky, Orit Goldschmidt, Eyal Zcharia, Ruth Atzmon, Zehava Rangini-Guatta, Michael Elkin, Tamar Peretz and Yael Friedmann, Mammalian heparanase: involvement in cancer metastasis, angiogenesis and normal development, Seminars in Cancer Biology, 2002, p. 121-129, vol. 12.

Yi Xiao, Jorg Kleeff, Xin Shi, Markus W. Buchler, and Herlmut Friess, Heparanase expression in hepatocellular carcinoma and the cirrhotic liver, Hepatology Research, Feb. 21, 2003, p. 192-198, vol. 26.

Eyal Zcharia, Shula Metzger, Tova Chajek-Shaul, Yael Friedmann, Orit Pappo, Ayelet Aviv, Michael Elkin, Iris Packer, Tamar Peretz and Israel Vlodavsky, Molecular Properties and Involvement of Hepanase in Cancer Progression and Mammary Gland Morphogenesis, Journal of Mammary Gland Biology and Neoplasia, 2001, p. 311-322, vol. 6.

Anna Zetser, Yulia Bashenko, Hua-Quan Miao, Israel Vlodavsky and Neta Ilan, Hepanase Affects Adhesive and Tumorigenic Potential of Human Glioma Cells, Cancer Research 63, 2003, p. 7733-7741.

Israel Vlodavsky, Orit Goldshmidt, Eyal Zcharia, Shula Metzger, Tova Chajek-Shaul, Ruth Atzmon, Zehava Guatta-Rangini, Yael Friedmann, Molecular properties and involvement of heparanase in cancer progression and normal development, Biochimie, 2001, p. 831-839, v:83.

Anna Zetser, Flonia Levy-Adam, Victoria Kaplan, Svetlana Gingis-Velitski, Yulia Bashenko, Shay Schubert, Moshe Y. Flugelman, Israel Vlodavsky and Neta Ilan, Processing and activation of latent heparanase occurs in lysosomes, Journal of Cell Science, 2003, p. 2249-2258, v:117.

Human Heparanase, Purification, Characterization, Cloning, and Expression, Minako Toyoshima et al, vol. 274, No. 34, Issue of Aug. 20. pp. 24153-24160, 1999 "The Journal of Biological Chemistry".

Identification and Characterization of Heparin/Heparan Sulfate Binding Domains of the Endoglycosidase Heparanase, Flonia Levy-Adam et al, vol. 280, No. 21, Issue of May 27, pp. 20457-20466, 2005, "The Journal of Biological Chemistry".

International Search Report published Aug. 4, 2005 for PCT/IL2005/000068 filed Jan. 20, 2005 (PCT/IL2005/000068 claims priority to U.S. Appl. No. 10/901,943).

International Preliminary Report on Patentablity published Jan. 5, 2006 for PCT/IL2005/000068 filed Jan. 20, 2005 (PCT/IL2005/000068 claims priority to U.S. Appl. No. 10/901,943).

Written Opinion of PCT/IL2005/000068 published Jul. 22, 2006 for PCT/IL2005/000068 filed Jan. 20, 2005 (PCT/IL2005/000068 claims priority to U.S. Appl. No. 10/901,943).

Avi Katz MD, David I. Van-Dijk MD, Helena Aingorn PHD, Arie Erman MD, Malcolm Davies MD, David Darmon MD, Hagit Hurvitz MD, and Israel Vlodavsky, Involvement of Human Heparanase in the Pathogenesis of Diabetic Nephropathy, Isr. Med. Assoc., Nov. 2002, p. 996-1002, vol. 4.

Andrea Koenig, Karin Norgard-Sumnicht, Robert Linhardt, and Ajit Varki, Differential Interactions of Heparin and Heparan Sulfate Glycosaminoglycans with the Selectins, J. clin. Invest., Inc., Feb. 1998, p. 877-889, vol. 101, No. 4.

Alexander Koliopanos, Helmut Friess, Jorg Kleeff, Xin Shi, Quan Liao, Iris Pecker, Israel Vlodavsky, Arthur Zimmermann, and Markus W. Buchler, Heparanase Expression in Primary and Metastatic Pancreatic Cancer, Cancer Research, Jun. 15, 2001, p. 4655-4659, vol. 61.

Vivki Levidiotis, Craig Freeman, Chris Tikellis, Mark E. Cooper, and David A. Power, Heparanase Is Involved in the Pathogenesis of Proteinuria as a Result of Glomerulonephritis, J. Am. Soc. Nephrol., 2004, p. 68-78, vol. 15.

Vicki Levidiotis, John Kanellis, Frank L. Ierino, and David A. Power, Increased expression of heparanase in puromycin aminonucleoside nephrosis, Kidney International, 2001, p. 1287-1296, vol. 60.

Flonia Levy-Adam, Hua-Quan Miao, Robert L. Heinrikson, Israel Vlodavsky, and Neta Ilan, Heterodimer formation is essential for heparanase enzymatic activity, Biochemical and Biophysical Research Communications, Jul. 21, 2003, p. 885-891, vol. 308.

Ofer Lider, Ehud Baharav, Joseph A. Mekori, Ted Miller, Yaakov Naparstek, Israel Vlodavsky, and Irun R. Cohen, Supression of Experimental Autoimmune Diseases and Prolongation of Allograft Survival by Treatment of Animals with Low Doses of Heparins, J. Clin. Invest., Mar. 1989, p. 752-756, vol. 83.

Dario Marchetti, Jane Reiland, Brad Erwin and Madhuchhanda Roy, Inhibitors of Heparanase Activity and Heparanase-Induced Angiogenesis By Suramin Analogues, Int. J. Cancer, 2003, p. 167-174, vol. 104.

Cristina Mateo, Ernesto Moreno, Kathryn Amour, Josefa Lombardero, William Harris, and Rolando Peres, Humanization of a mouse monoclonal antibody that blocks the epidermal growth factor receptor: recovery of antagonistic activity, Immunothechnology 3, Jan. 31, 1997, p. 71-81, vol. 3.

Edward McKenzie, Kathryn Young, Margaret Hircock, James Bennett, Maina Bhaman, Robert Felix, Paul Turner, Alasdair Stamps, David McMillan, Giles Saville, Stanley Ng, Sean Mason, Daniel Snell, Darren Schofield, Haiping Gong, Reid Townsend, John Gallagher, Martin Page, Raj Parekh, and Colin Stubberfield, Biochemical characterization of the heterodimer form of human heparanase (Hpa1) protein expressed in insect cells, Biochemical J., 2003, p. 423-435, vol. 373.

* cited by examiner

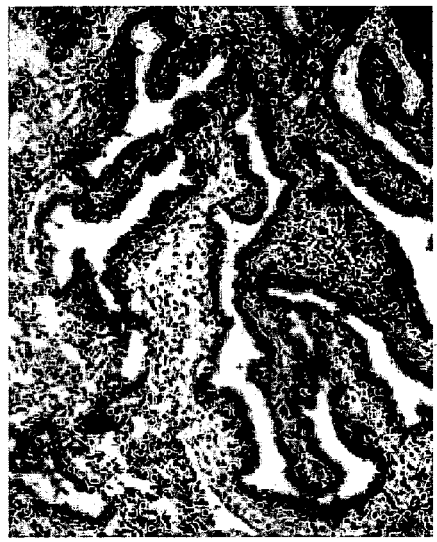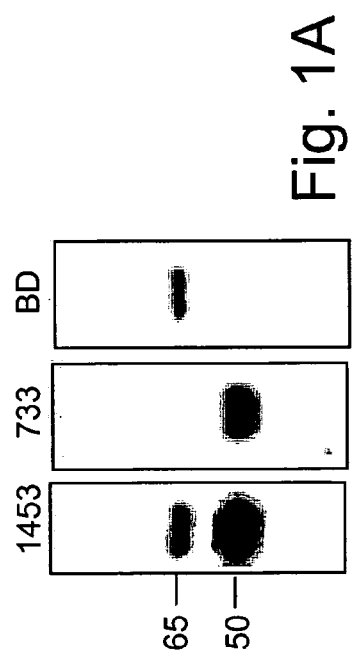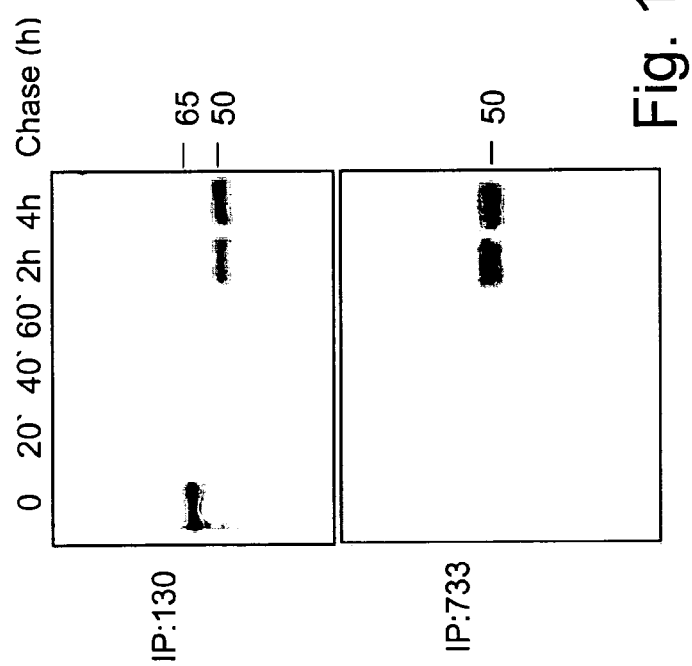
Fig. 1A  Fig. 1B  Fig. 1C

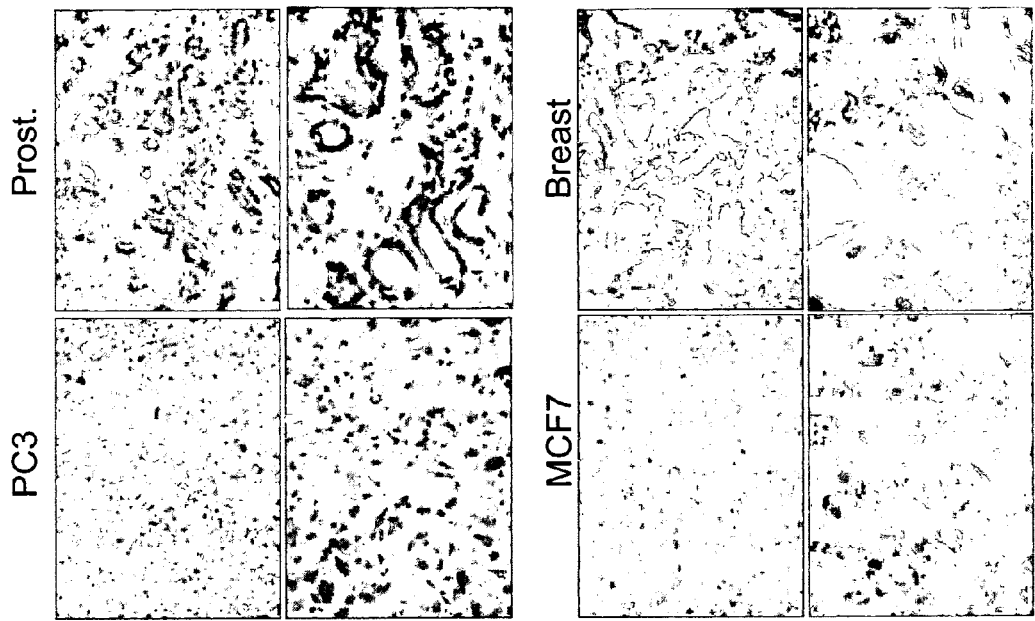
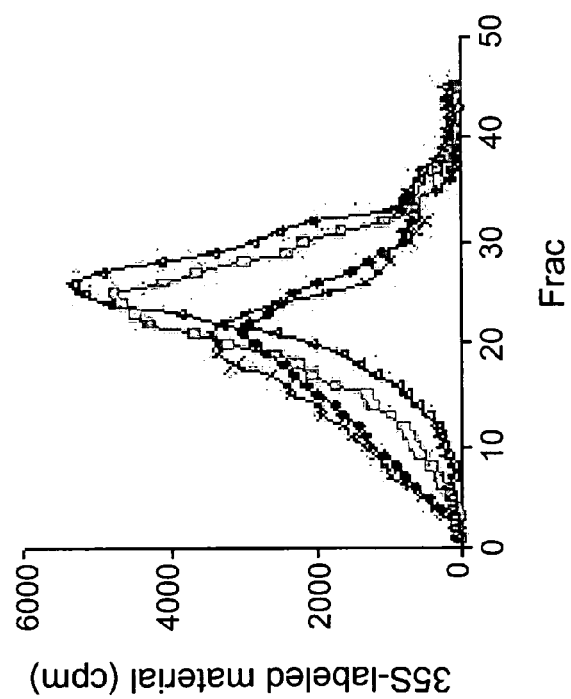
Fig. 2A
Fig. 2B
Fig. 2C

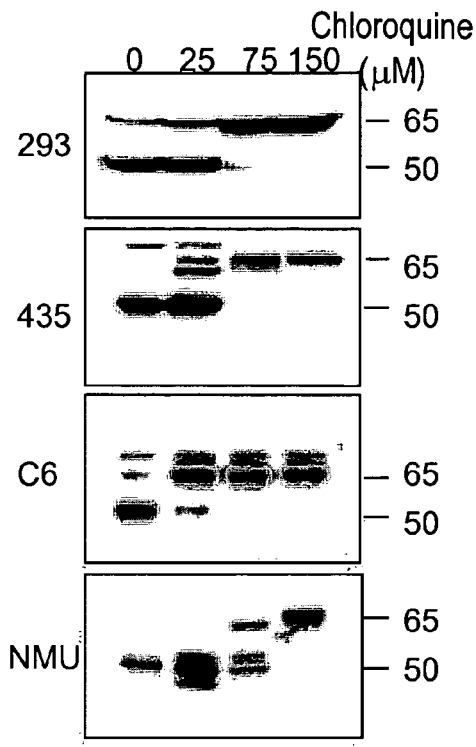
Fig. 4A
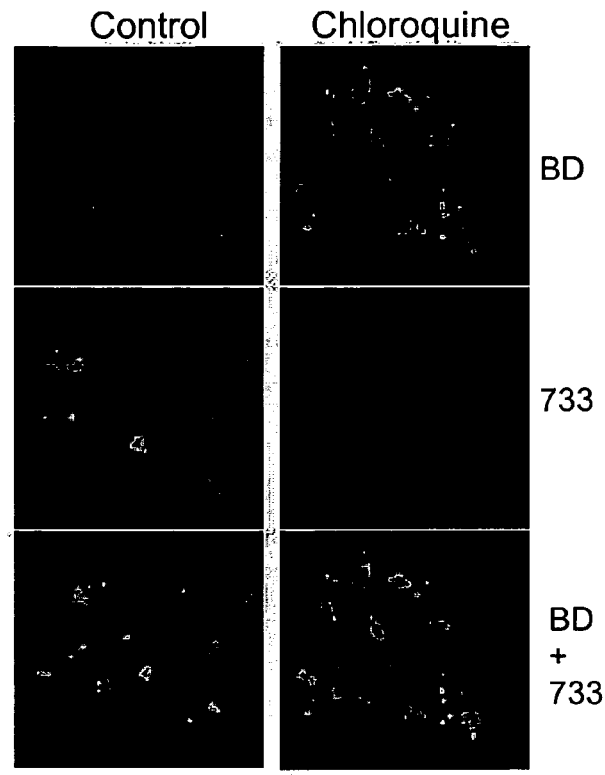
Fig. 4D
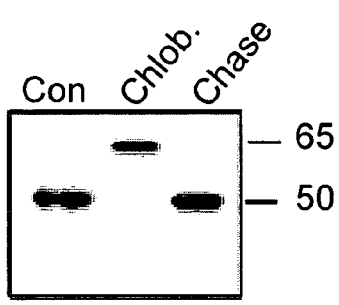
Fig. 4B
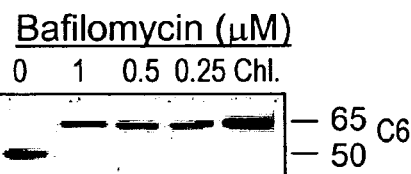
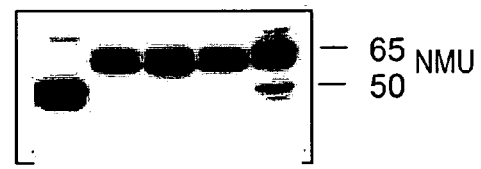
Fig. 4E
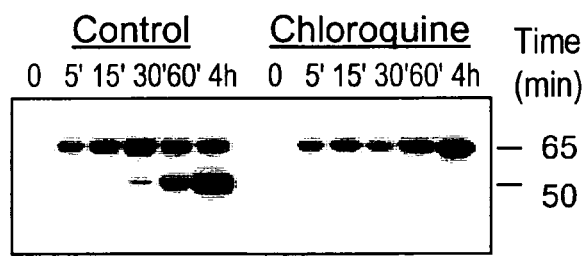
Fig. 4C

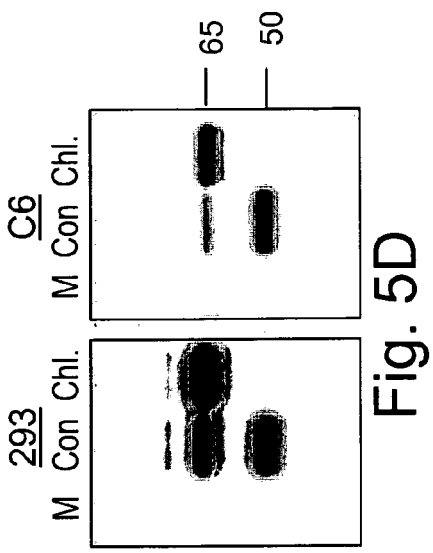
Fig. 5C
Fig. 5D
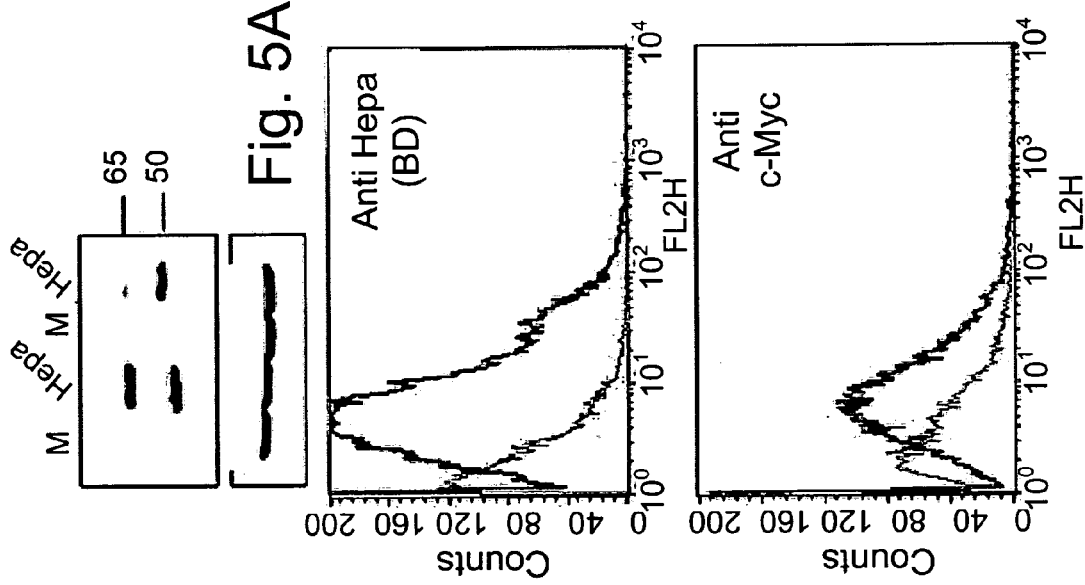
Fig. 5A
Fig. 5B

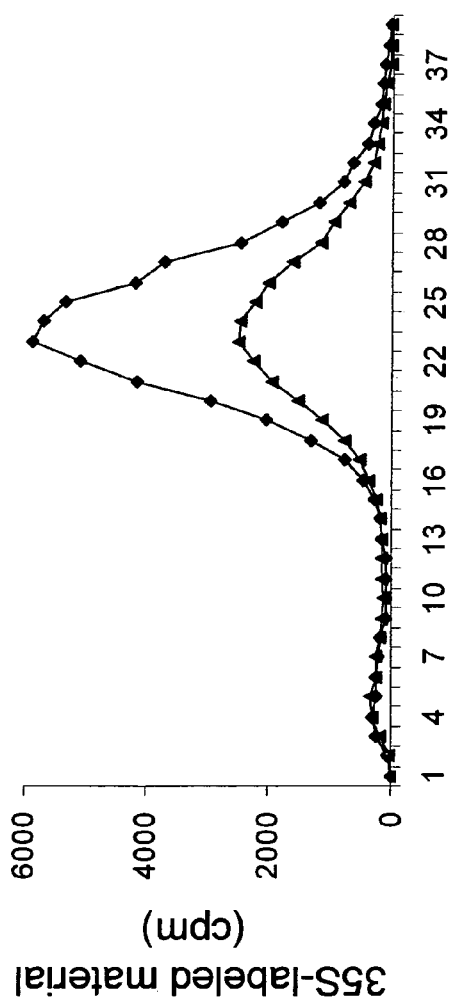
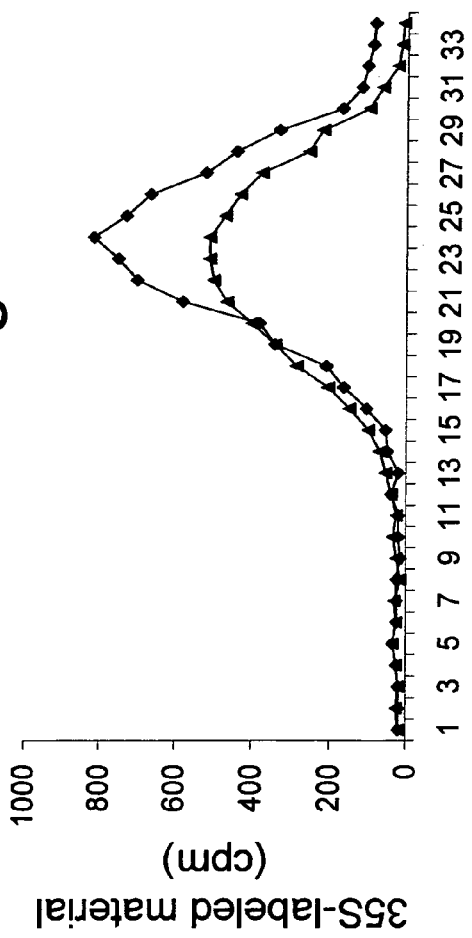

SUBSTANCES DIRECTED AGAINST A SPECIFIC SEQUENCE ESSENTIAL FOR HEPARANASE CATALYTIC ACTIVITY AND USES THEREOF AS HEPARANASE INHIBITORS

BACKGROUND OF THE INVENTION

1. Field of the Invention

The present invention relates to specific inhibitors of heparanase catalytic activity, directed to an amino acid sequence derived from the N-terminus sequence of the 50 Kd cleavage product of heparanase precursor. More particularly, the invention relates to an amino acid sequence derived from amino acid residues $Lys^{158}$-$Asp^{171}$ of human heparanase and any functional fragments thereof, and the use of said sequence in a screening method for specific heparanase inhibitors. The invention further provides compositions and methods comprising said heparanase inhibitors for the treatment of heparanase related disorders.

2. Prior Art

Throughout this application various publications are referenced to. It should be appreciated that the disclosure of these publications in their entireties are hereby incorporated into this application in order to more fully describe the state of the art as known to those skilled therein as of the date of the invention described and claimed herein.

Heparanase is an endo-β-D-glucuronidase involved in cleavage of heparan sulfate (HS) chains, and hence participates in extracellular matrix (ECM) degradation and remodeling. Heparanase activity has been traditionally correlated with the metastatic potential of tumor-derived cell types [Nakajima, M. et al., J. Cell. Biochem. 36, 157-167 (1998); Vlodavsky, I. et al., Nat. Med. 5, 793-802 (1999); Parish, C. R. et al., Biochem. Biophys. Acta 1471, M99-M108 (2001); Vlodavsky, I. and Friedmann Y., J. Clin. Invest. 108, 341-347 (2001)]. Similarly, heparanase has been shown to facilitate cell invasion associated with autoimmunity, inflammation and angiogenesis [Vlodavsky, I. et al., Invasion & Metastasis 12, 112-127 (1992); Dempsey, L. et al., Trends Biol. Sci. 25, 349-351 (2000a); Parish (2001) ibid.]. More recently, heparanase upregulation was detected in a variety of human primary tumors correlating, in some cases, with increased tumor vascularity and poor postoperative survival [El-Assal, O. N. et al., Clin. Cancer Res. 7, 1299-1305 (2001); Gohji, K. et al., Int. J. Cancer 95, 295-301 (2001); Koliopanos, A. et al., Cancer Res. 61, 4655-4659 (2001); Rohloff, J. et al., J. Cancer 86, 1270-1275 (2002)]. In addition, increased heparanase expression has been noted in kidney [Levidiotis, V. et al., Kidney Int. 60, 1287-1296 (2001)], liver [Xiao, Y. et al., Hepatology Res. 26, 192-198 (2003)] and diabetic [Katz, A. et al., Isr. Med. Assoc. 4, 996-1002 (2002)] disorders. In the latter case, increased heparanase activity in patient's urine has been detected, suggesting that heparanase may serve as an early marker in diabetes and potentially other pathologies such as tumor metastasis [Goldshmidt, O. et al., Proc. Natl. Acad. Sci. USA 99, 10031-10036 (2002)]. Increased heparanase activity in urine and possibly other body fluids strongly implies that heparanase is a secreted enzyme. In addition, exogenously added and endogenous heparanase were localized to endosomes and lysosomes [Nadav, L. et al., J. Cell Sci. 115, 2179-2187 (2001); Goldshmidt (2002) ibid.].

The heparanase cDNA encodes for a polypeptide of 543 amino acids that appears as a ~65 kDa protein in SDS-PAGE analysis. The protein undergoes proteolytic processing which is likely to occur at two potential cleavage sites, $Glu^{109}$-$Ser^{110}$ and $Gln^{157}$-$Lys^{158}$, yielding an 8 kDa polypeptide at the N-terminus, a 50 kDa polypeptide at the C-terminus and a 6 kDa linker polypeptide that resides in-between [Fairbanks, M. B. et al., J. Biol. Chem. 274, 29587-29590 (1999); Parish (2001) ibid.]. Recently published observations clearly demonstrated that the active heparanase enzyme exists as a heterodimer composed of the 8 kDa polypeptide non-covalently associated with the 50 kDa heparanase subunit, and that heterodimer formation is necessary and sufficient for heparanase enzymatic activity [Levy-Adam, F. et al., Biochem. Biophy. Res. Comm. 308, 885-891 (2003); McKenzie, E. et al., Biochemical J. 373, 423-435 (2003)]. Nevertheless, currently available anti-heparanase antibodies do not distinguish between the latent 65 kDa heparanase precursor and the 50 kDa active enzyme. Thus, specific localization of the latent and active heparanase forms within the cell could not be determined.

SUMMARY OF THE INVENTION

The inventors have rationalized that heparanase processing may involve conformational changes that are likely to alter antibodies reactivity. More specifically, the inventors hypothesized that cleavage at the $Gln^{157}$-$Lys^{158}$ site that ultimately results in formation of the 50 kDa heparanase subunit will generate an epitope specific for the 50 kDa heparanase form. The inventors have therefore prepared and characterized an antibody (designated #733) that was raised against a 14 amino acid peptide mapped at the N-terminus region of the 50 kDa heparanase ($Lys^{158}$-$Asp^{171}$) as disclosed by the present invention. As shown herein, this antibody preferentially recognizes the active 50 kDa heparanase form by means of immunoblotting and immunoprecipitation, and labels heparanase in archive paraffin sections subjected to immunohistochemistry. Moreover, this antibody neutralizes the enzymatic activity of heparanase, suggesting that the N-terminus region of the 50 Kd subunit molecule participates in a three dimensional organization required for proper folding and enzymatic activity. In addition, the inventors show herein, that synthetic peptides derived from the N-terminus region of the 50 Kd subunit of heparanase, comprising the amino acid sequence of amino acid residues from 158 to 171 (also denoted by SEQ ID NO: 1), completely blocked heparanase catalytic activity.

Moreover, heparanase mutated molecule having deletion of this particular 14 amino acid sequence (SEQ ID NO: 1), was shown by the present inventors as being devoid of heparanase catalytic activity.

The results of the present invention clearly indicate that the amino acid sequence comprising residues 158 to 171 is essential for heparanase catalytic activity and therefore may be used as a target sequence for identifying potential novel heparanase inhibitors.

It is therefore an object of the invention to provide a method of screening for a substance which specifically binds to an amino acid sequence derived from the N-terminus region of the 50 Kd subunit of heparanase and is capable of inhibiting heparanase glycosidase catalytic activity, by using the isolated amino acid sequence of the invention (as denoted also by SEQ ID NOs: 1 and 2). The invention further provides an antibody which specifically binds to the sequence of the invention and therefore inhibits heparanase catalytic activity. The invention provides compositions and methods using said antibody as heparanase inhibitor.

The results of the present invention clearly indicate that the amino acid sequence comprising residues 158-171 of SEQ ID NO:1 is essential for heparanase catalytic activity and therefore may be used as a target sequence for identifying potential novel heparanase inhibitors.

Another object of the invention is to provide heparanase mutated molecule having deletion of the N-terminus region of the 50 Kd subunit being devoid of heparanase glycosidase activity.

These and other objects of the invention will become apparent as the description precede.

In a first aspect, the invention relates to an amino acid sequence derived from the N-terminus region of the 50 Kd subunit of heparanase. As clearly demonstrated by the following Examples, this sequence is required for heparanase catalytic activity, by enabling appropriate folding of the active heparanase molecule, or alternatively, by being involved with the substrate recognition.

In one preferred embodiment, the amino acid sequence of the invention comprises amino acid residues $Lys^{158}$ to $Asp^{171}$ of human heparanase or any functionally equivalent fragment, derivative, and variant thereof. In another specifically preferred embodiment, the amino acid sequence of the invention comprises the amino acid sequence of any one of SEQ ID NO: 1 and SEQ ID NO: 2 and any functionally equivalent fragment, derivative, and variant thereof.

In a second aspect, the invention relates to an isolated and purified peptide comprising an amino acid sequence derived from the N-terminus region of the 50 Kd subunit of heparanase. The peptide of the invention is capable of competing with the corresponding sequence within the heparanase molecule and thereby inhibiting heparanase catalytic activity.

According to one embodiment, the peptide of the invention comprises the amino acid residues $Lys^{158}$ to $Asp^{171}$ of human heparanase or any functionally equivalent fragment, derivative, and variant thereof. Preferably, the peptide of the invention comprise the amino acid sequence as denoted by any one of SEQ ID NO: 1 and SEQ ID NO: 2 or any functionally equivalent fragment, derivative, and variant thereof.

A further aspect of the invention relates to a composition for the inhibition of heparanase glycosidase catalytic activity, comprising as an active ingredient the isolated and purified peptide of the invention. This composition optionally further comprises a pharmaceutically acceptable carrier, diluent, excipient and/or additive.

The invention further provides for a pharmaceutical composition for the treatment or the inhibition of a process or a pathologic disorder associated with heparanase catalytic activity. Such composition may comprise as an active ingredient, the isolated and purified peptide of the invention. It should be noted that this composition may optionally further comprise a pharmaceutically acceptable carrier, diluent, excipient and/or additive.

Accordingly, the pharmaceutical composition of the invention is intended for the treatment of a process associated with heparanase catalytic activity such as, angiogenesis, tumor formation, tumor progression and tumor metastasis. Alternatively and additionally, the composition of the invention may be applicable for the treatment of a pathologic disorder, such as a malignant proliferative disorder, for example, solid and non-solid tumor such as carcinoma, sarcoma, melanoma, leukemia and lymphoma, an inflammatory disorder, an autoimmune disorder and a kidney disorder.

In a further aspect the invention provides the use of the isolated and purified peptide of the invention, for the inhibition of heparanase glycosidase catalytic activity.

Still further, the invention provides for the use of the isolated and purified peptide of the invention, in the preparation of a composition for the inhibition of heparanase glycosidase catalytic activity.

The invention further relates to the use of the isolated and purified peptide of the invention, in the preparation of a pharmaceutical composition for the treatment or the inhibition of a process or a pathologic disorder associated with heparanase glycosidase catalytic activity. Such composition optionally further comprising a pharmaceutically acceptable carrier, diluent, excipient and/or additive.

According to a preferred embodiment, the use of such peptide according to the invention is for the preparation of a pharmaceutical composition for the inhibition or treatment of a process associated with heparanase catalytic activity, such as, angiogenesis, tumor formation, tumor progression and tumor metastasis. In another embodiment, the use is for a pathologic disorder such as a malignant proliferative disorder, for example, solid and non-solid tumor selected from the group consisting of carcinoma, sarcoma, melanoma, leukemia and lymphoma. The use according to another embodiment may be for the treatment of an inflammatory disorder, an autoimmune disorder or a kidney disorder.

The invention further provides for a method for the inhibition of heparanase glycosidase catalytic activity comprising the step of in vivo or in vitro contacting heparanase under suitable conditions, with an inhibitory effective amount of the isolated and purified peptide of the invention, or with a composition comprising the same.

Still further, the invention provides a method for the inhibition of heparanase glycosidase catalytic activity in a subject in need thereof. This method comprises the step of administering to the subject an inhibitory effective amount of the isolated and purified peptide of the invention, or of a composition comprising the same.

In another embodiment, the invention relates to a method for the inhibition or the treatment of a process or a pathologic disorder associated with heparanase glycosidase catalytic activity. Such method comprises the step of administering to a subject in need thereof a therapeutically effective amount of the isolated and purified of the invention, or of a composition comprising the same.

In another aspect, the invention relates to a method of screening for a test substance which specifically binds to an amino acid sequence derived from the N-terminus region of the 50 Kd subunit of heparanase and is capable of inhibiting heparanase glycosidase catalytic activity. The screening method of the invention comprises the steps of: (a) obtaining a test substances which bind to the 50 Kd subunit of heparanase; (b) selecting from the 50 Kd subunit of heparanase-binding substances obtained in step (a), a candidate substance that specifically binds to a sequence comprising amino acid residues $Lys^{158}$ to $Asp^{171}$ of heparanase, preferably, the amino acid sequence of the invention; and (c) evaluating the candidate substance obtained in step (b) by determining the inhibitory effect of said substance on the glycosidase catalytic activity of heparanase.

The present invention further provides a method of preparing a therapeutic composition for the treatment of a process or a pathologic disorder associated with heparanase glycosidase catalytic activity in a mammalian subject. Such method comprises the steps of: (a) identifying a substance that is capable of specifically inhibiting heparanase glycosidase catalytic activity by binding to an amino acid sequence derived from the N-terminus region of the 50 Kd subunit of heparanase, preferably, by the screening method of the invention; and (b)

admixing said candidate substance with at least one of a pharmaceutically acceptable carrier, diluent, excipient and additive.

In yet another aspect, the invention relates to a substance which specifically binds to an amino acid sequence derived from the N-terminus region of the 50 Kd subunit of heparanase and is capable of inhibiting heparanase glycosidase catalytic activity. Preferably, the amino acid sequence comprises the amino acid residues $Lys^{158}$ to $Asp^{171}$ of human heparanase or any functionally equivalent fragment, derivative and variant thereof, most preferably, the amino acid sequence defined by the invention.

According to a specifically preferred embodiment, the substance of the invention is obtained by the screening method of the invention.

The invention therefore provides a composition for the inhibition of heparanase glycosidase catalytic activity, and a pharmaceutical composition for the treatment or the inhibition of a process or a pathologic disorder associated with heparanase catalytic activity. These compositions comprise as an active ingredient the substance of the invention which specifically binds to the amino acid sequence of the invention and is capable of inhibiting heparanase glycosidase catalytic activity, said composition optionally further comprising a pharmaceutically acceptable carrier, diluent, excipient and/or additive.

In yet another aspect, the invention relates to the use of the substance of the invention for the inhibition of heparanase glycosidase catalytic activity, in the preparation of a composition for the inhibition of heparanase glycosidase catalytic activity, and in the preparation of a pharmaceutical composition for the treatment or the inhibition of a process or a pathologic disorder associated with heparanase glycosidase catalytic activity.

The invention further relates to method for the inhibition of heparanase glycosidase catalytic activity comprising the step of in vivo or in vitro contacting heparanase, under suitable conditions, with an inhibitory effective amount of the substance of the invention, or with a composition comprising the same.

In another embodiment, the invention relates to a method for the inhibition of heparanase glycosidase catalytic activity in a subject in need thereof, and preferably, for the treatment of a process or a pathologic disorder associated with heparanase glycosidase catalytic activity. These methods comprise the step of administering to said subject an inhibitory effective amount of the substance of the invention, or of a composition comprising the same.

In yet another aspect, the invention relates to an antibody which specifically recognizes the amino acid sequence of the invention. In a specifically preferred embodiment, such antibody specifically recognizes the active form of heparanase.

In yet another specifically preferred embodiment, the antibody of the invention is capable of inhibiting heparanase glycosidase catalytic activity.

It should be appreciated that the antibody of the invention may be a polyclonal or a monoclonal antibody. According to a particularly preferred embodiment, the antibody of the invention is an affinity-purified polyclonal antibody designated #733.

The invention further relates to compositions for the inhibition of heparanase glycosidase catalytic activity and for the treatment or the inhibition of a process or a pathologic disorder associated with heparanase catalytic activity. These compositions comprise as an active ingredient, the antibody of the invention and most preferably, the affinity purified #733 antibody.

The invention further provide the use of the antibody of the invention, and most preferably, the affinity purified antibody #733 of the invention, for the inhibition of heparanase glycosidase catalytic activity, for the preparation of a composition for the inhibition of heparanase glycosidase catalytic activity and for the preparation of a pharmaceutical composition for the treatment or the inhibition of a process or a pathologic disorder associated with heparanase glycosidase catalytic activity.

The invention further provides a method for the inhibition of heparanase glycosidase catalytic activity comprising the step of in vivo or in vitro contacting heparanase under suitable conditions, with an inhibitory effective amount of the antibody of the invention, or with a composition comprising the same.

According to another embodiment, the invention relates to a method for the inhibition of heparanase glycosidase catalytic activity in a subject in need thereof, and to a method for the inhibition or the treatment of a process or a pathologic disorder associated with heparanase glycosidase catalytic activity. The methods of the invention comprise the step of administering to a subject in need thereof a therapeutically effective amount of an antibody, preferably, the antibody of the invention, or of a composition comprising the same.

In a further embodiment of this aspect, the invention relates to a method for the diagnosis of a process or a pathologic disorder associated with heparanase glycosidase catalytic activity in a mammalian subject comprising: (a) providing a sample of said subject; (b) contacting said sample with the antibody of the invention; (c) removing any unbound antibody; and (d) detecting the extent of reaction between said antibody and said heparanase active form present in said sample by suitable means.

In yet a further aspect, the invention relates to a nucleic acid construct comprising a polynucleotide sequence encoding a heparanase-derived polypeptide, preferably, a human heparanase-derived polypeptide, devoid of all or part of amino acid residues $Lys^{158}$ to $Asp^{171}$ of heparanase and being devoid of heparanase catalytic activity, which construct optionally further comprises operably linked regulatory elements.

According to a specifically preferred embodiment, the polypeptide of the invention has the amino acid sequence as denoted by SEQ ID NO: 4 and is encoded by a nucleic acid sequence denoted by SEQ ID NO:3.

The invention further provide an expression vector comprising the amino acid construct of the invention and a host cell transformed or transfected with the expression vector of the invention.

The invention further provides a mutated recombinant protein comprising heparanase-derived polypeptide devoid of amino acid residues $Lys^{158}$ to $Asp^{171}$ of human heparanase and therefore being devoid of heparanase endoglycosidase catalytic activity. Specifically, the mutant heparanase molecule of the invention comprises the amino acid sequence substantially as denoted by SEQ ID NO: 4, encoded by the nucleic acid sequence substantially as denoted by SEQ ID NO: 3.

The invention will be further described on the hand of the following figures, which are illustrative only and do not limit the scope of the invention which is defined by the appended claims.

BRIEF DESCRIPTION OF THE FIGURES

FIG. 1A-1C Characterization of Antibody #733 Specificity

FIG. 1A. Immunoblot analysis—Lysates of heparanase transfected HEK-293 cells were resolved by SDS-PAGE and blots were probed with antibody #1453 (left panel), #733 (middle panel) and anti heparanase monoclonal antibody purchased from Becton-Dickinson (BD, right panel).

FIG. 1B. Metabolic-labeling followed by immunoprecipitation—Heparanase-transfected CHO cells were pulsed for 20 minutes with [$^{35}$S]-methionine (0) and then chased for the indicated time intervals in complete growth medium containing an access of cold methionine. Equal volumes of cell lysate samples were subjected to immunoprecipitation (IP) with mAb 130 (upper panel) or antibody #733 (bottom panel), as described in 'Experimental procedures'.

FIG. 1C. Immunohistochemistry—Five micron placenta sections were subjected to immunostaining with antibody #733, as described in 'Experimental procedures'.

FIGS. 2A-2C Heparanase Activity and Localization in Cell Xenografts and Tumor Biopsies FIG. 2A. Heparanase activity—Cell extracts of MCF7 (♦), MDA-MB-435 (▲), PC3 (×) and LnCap (■) cells (1×10$^6$) were incubated (4 hours, 37° C.) with sulfate labeled ECM and heparanase activity was determined as described in 'Experimental procedures', for each fraction (frac.).

FIGS. 2B-2C. Staining of prostate and breast xenografts and tumor biopsies with antibody #733. PC3 (B, a-b) xenograft, prostate biopsy (B, c-d), MCF7 (C, a-b) xenograft and breast cancer biopsy (C, c-d) sections were subjected to antigen retrieval and immunostaining with antibody #733. Original magnifications: 2B, *a, c* and 2C, *a, c*×20; 2B, *b, d* and 2C, *b, d*×100.

Figure 3:
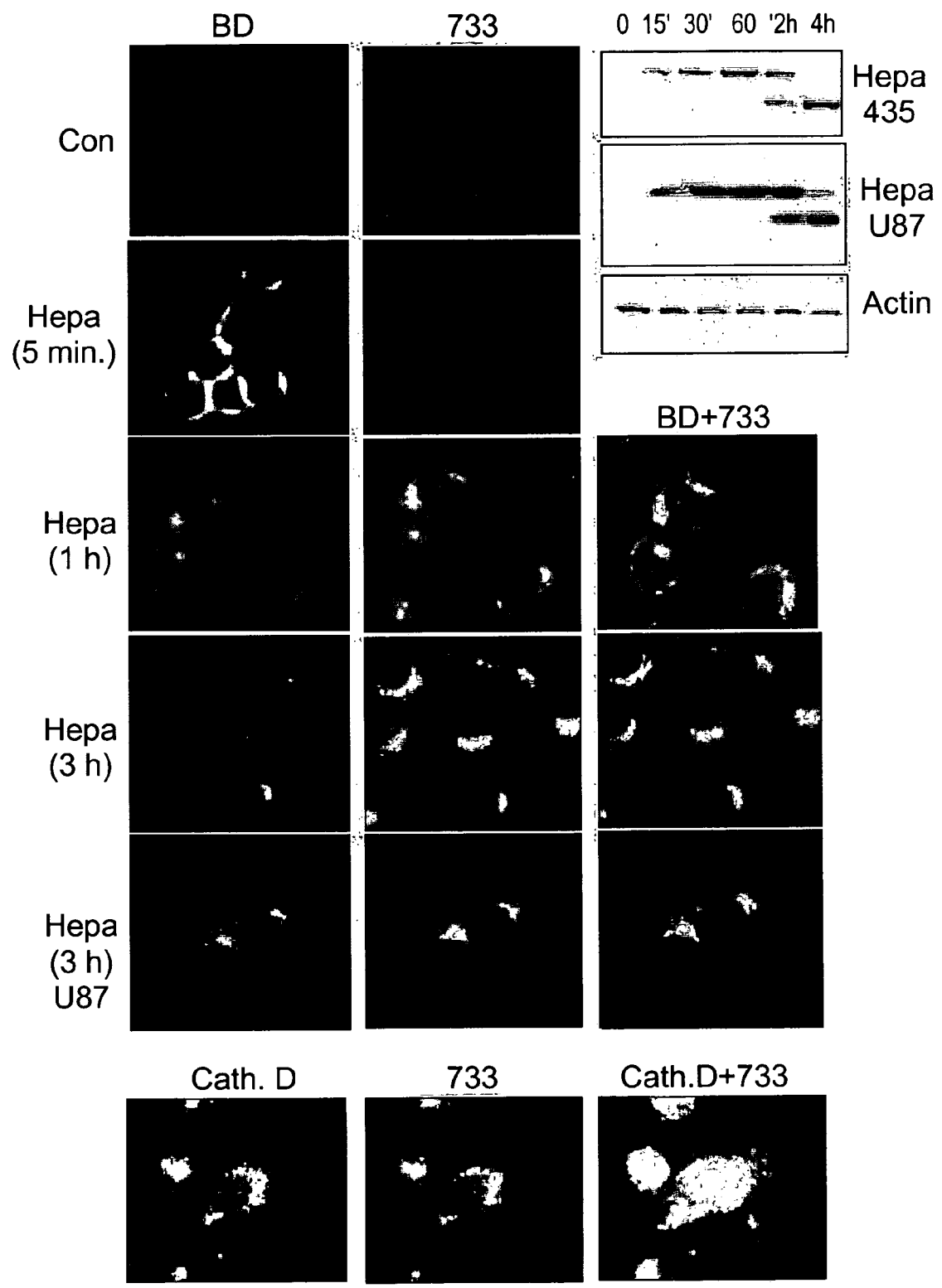
FIG. 3 Heparanase Uptake, Processing and Localization in Human MDA-435 Breast Cancer and U87 Glioma Cells MDA-435 cells were left untreated (upper panel) or incubated with the 65 kDa heparanase precursor (5 μg/ml) for 5 minutes (second panel), 1 hour (third panel) or 3 hours (fourth panel) and stained with monoclonal anti-heparanase antibody (BD, left panels, red) and with antibody #733 (middle panels, green). Merge images are shown in the right panels. U87 cells were incubated with heparanase for 3 hours and similarly stained (fifth panel). Original magnifications: ×100.

Inset. Heparanase uptake and processing, as evident by immunoblotting. MDA-435 (upper panel) and U87 glioma cells (second panel) were left untreated (0) or incubated with the 65 kDa heparanase precursor. At the indicated time points, cells were washed and total cell lysates were subjected to SDS-PAGE followed by immunoblotting with antibody #1453 (first and second panels), or with anti-actin antibody (third panel). Hepa (heparanase), Cath. D (Cathapsin D). Abbreviations: hepa (heparanase).

FIG. 4A-4E Heparanase Processing is Inhibited by Lysosomal Proteinase Inhibitors FIG. 4A. Heparanase-transfected 293 (upper panel), MDA-435 breast (second panel), C6 glioma (third panel) and NMU (fourth panel) cells were left un-treated (0) or incubated for 20 hours with the indicated concentrations (μM) of chloroquine. Total cell lysates were immunoblotted with anti-heparanase antibody #1453. Note a dose-response inhibition of heparanase processing and accumulation of the un-processed 65 kDa heparanase precursor.

FIG. 4B. Chloroquine treatment is reversible—Heparanase-transfected C6 glioma cells were left untreated (Con) or treated with 50 μM chloroquine for 20 hours. Cells were then lysed (Chloro) or washed and chased for additional 24 hours with chloroquine-free medium (Chase). Total cell lysates were then analyzed for heparanase processing by immunoblotting as above. Note re-appearance of the processed 50 kDa heparanase form upon chloroquine removal.

FIG. 4C. Uptake studies—U87 glioma cells were left untreated (Control) or pre-treated with 100 μM chloroquine (Chloroquine) for 2 hours. The latent 65 kDa heparanase protein was then added for the indicated time points and total cell lysates were analyzed for heparanase processing by immunoblotting as above. Note complete inhibition of exogenously-added heparanase upon chloroquine pre-treatment.

FIG. 4D Uptake studies—U87 glioma cells were left untreated (Control) or incubated with chloroquine (100 μM) for 2 hours, followed by the addition of the 65 kDa heparanase protein for additional 2 hours. Cells were then fixed and immunostained with anti heparanase monoclonal antibody (BD, upper panel) and anti heparanase (733, second panel) antibodies. Merge images are shown at the third panel. Note the complete absence of heparanase processing as evident by the lack of reactivity with the #733 antibody upon chloroquine treatment (second panel, right), and the accumulation of the latent heparanase form in large vesicles.

FIG. 4E. Heparanase-transfected C6 glioma (upper panel) and NMU (lower panel) cells were left untreated (0) or incubated with the indicated concentration (nM) of bafilomycin A1 or chloroquine (Chl, 50 μM) for 20 hours. Total cell lysates were analyzed by immunoblotting as above. Note complete inhibition of heparanase processing upon bafilomycin treatment.

FIGS. 5A-5D Processing of Membrane-Targeted Heparanase is Chloroquine Sensitive

FIG. 5A. Expression of membrane-targeted heparanase in stable-transfected 293 and C6 cells—Control (M) and heparanase (Hepa) transfected cells were lysed and subjected to immunoblot analysis with anti heparanase antibody #1453 (upper panel) or anti actin antibodies (lower panel). 293 cells expressing the membrane-targeted heparanase gene construct were analyzed by FACS (FIG. 5B) with anti heparanase monoclonal antibody (BD, upper panel) and anti c-Myc epitope tag antibodies (lower panel), or stained by immunofluorescence (FIG. 5C) with anti heparanase monoclonal antibodies (BD). Note heparanase accumulation at areas of cell-cell junctions in sparse cultures (C, upper panel) and exclusive localization at the cell borders in confluent cells (C, lower panel).

FIG. 5D. Processing of membrane-targeted heparanase is chloroquine-sensitive. 293 (left panel) and C6 (right panel) cells stable transfected with the membrane-targeted heparanase gene construct were left untreated (Con) or treated for 20 hours with 100 μM chloroquine (Chl). Total cell lysates were immunoblotted with anti heparanase antibody #1453. Untransfected cell lysates were included as control (M).

FIGS. 6A-6B Antibody 733 Inhibits Heparanase Enzymatic Activity

FIG. 6A. Purified, active heparanase (20 ng) was added to 1 ml RPMI medium and incubated with affinity-purified antibody #733 (10 μg, ▲), or rabbit IgG (♦) for 1 hour on ice, followed by 1 hour incubation with $^{35}$S-labeled ECM. Heparanase activity was determined as described in 'Experimental procedures'.

FIG. 6B. Heparanase-transfected 293 cells (2×10$^5$) were plated on $^{35}$S-labeled ECM in the presence of affinity-purified antibody #733 (10 μg/ml, ▲) or control rabbit IgG (♦) for 2 hours. The incubation medium containing sulfate labeled degradation fragments was subjected to gel filtration on a Sepharose CL-6B column.

Figure 7:
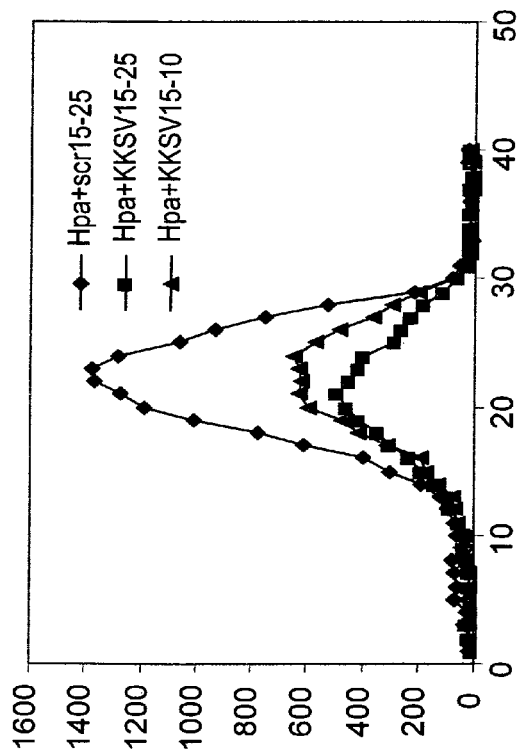

FIG. 7 15 Amino Acid Located at the N-Terminal Region of the 50 kDa Heparanase Protein are Crucial for its Enzymatic Activity A Purified, recombinant active heparanase (40 ng) was incubated (2 h, pH 7) with 10 μg (▲) or 25 μg (■) of a peptide containing the amino acid sequence of residues 158 to 171, or with a control, scrambled, peptide (♦). Note a dose-responsive inhibition of heparanase activity upon treatment with the 158-171 peptide.

Figure 8:
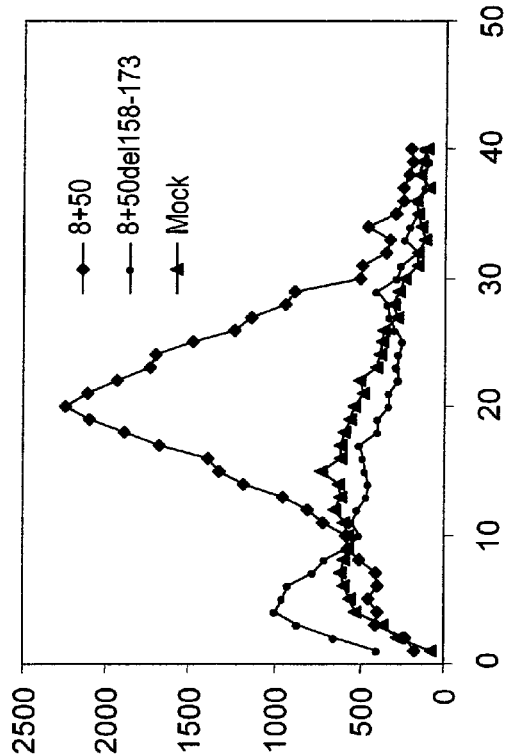

FIG. 8 Deletion Studies 293 cells were transfected with the 8 kDa and the wild type 50 kDa heparanase subunit (♦, 8+50) or the 50 kDa subunit in which amino acids 158-172 were deleted (●, 8+50 del) and heparanase activity was evaluate compared with control, mock transfected cells (▲, Mock). Note complete inhibition of heparanase activity upon deletion of the N-terminal, 158-172, sequence.

DETAILED DESCRIPTION OF PREFERRED EMBODIMENTS OF THE INVENTION

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al., (eds.) 3rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al., (eds), John Wiley & Sons. Inc., New York, N.Y.

Traditionally correlated with the metastatic potential of tumor-derived cells, heparanase up-regulation has been documented in an increasing number of primary human tumors [Zcharia, E. et al., J. Mammary Gland Biol. Neoplasia 6, 311-322 (2001); Vlodavsky, I. et al., Sem. Cancer Biol. 12, 121-129 (2002)]. More recently, increased heparanase expression was observed in several other disorders such as nephrosis [Levidiotis (2001) ibid.] and cirrhosis [Xiao (2003) ibid.]. The role that heparanase may play in these and other pathologies [Dempsey, L. et al., Glycobiology 10, 467-475 (2000b)] is only poorly understood. Moreover, heparanase expression is not restricted to pathological conditions and high levels of activity have long been found in placenta and more recently in the skin [Bernard, D. et al., J. Invest. Dermatol. 117, 1266-1273 (2001)] and other tissues [Dempsey (2000a) ibid.]. Specific heparanase inhibitors are expected to provide pivotal tools for studying heparanase functions under normal and pathological conditions. Currently available heparanase inhibitors are various sulfated poly- and oligosaccharides such as heparin fragments, laminaran sulfate and PI-88 [Miao H-Q. et al., Int. J. Cancer 83, 424-431 (1999); Parish, C. R. et al., Can. Res. 59, 3433-3441 (1999)]. These compounds were shown to inhibit heparanase activity and exhibit anti-metastatic and anti-angiogenic effects [Miao (1999) ibid.; Parish (1999) ibid.; Vlodavsky, I. et al., Invasion Metastasis 14, 290-302 (1994)]. Nevertheless, laminaran sulfate and species of heparin also inhibit bFGF binding to its receptor, resulting in inhibition of endothelial cell proliferation [Hoffman, R. et al., J. Cell Sci. 108, 3591-3598 (1995)] and angiogenesis [Hoffman, R. et al., J. Cell Sci. 108, 3591-3598 (1996)].

These compounds also inhibit selectin mediated cell adhesion [Koenig, A. et al., J. Clin. Invest. 101, 877-889 (1998); Varki, N. M. and Varki, A. Sem. Throm. Hemos. 28, 53-66 (2002)]. The lack of specificity makes interpretation questionable when using these and other polysulfated reagents [Nakajima, M. et al., J. Biol. Chem. 266, 9661-9666 (1991); Marchetti, D. et al., Int. J. Cancer. 104, 167-174 (2003)].

Therefore, there is need to isolate and characterize specific heparanase inhibitors, which specifically block heparanase catalytic activity. As will be described hereinafter, it has now been found that preferred specific inhibitors should be directed to a particular target region within the active heparanase molecule.

The present invention discloses characterization of an amino acid sequence derived from the N-terminal region of the 50 Kd subunit of heparanase and comprises amino acid residues $Lys^{158}$ to $Asp^{171}$ of heparanase. This sequence is shown by the present invention as essential for heparanase catalytic activity, most likely by participating in substrate binding or by conferring appropriate active conformation of heparanase.

As shown by the present invention, such sequence may be used as a target for substances such as antibodies, which bind this sequence and thereby disturb heparanase catalytic activity and therefore may be used as specific and potent inhibitors of heparanase.

Thus, in a first aspect, the invention relates to an amino acid sequence derived from the N-terminus region of the 50 Kd subunit of heparanase. As clearly demonstrated by the following Examples, this sequence is required for heparanase catalytic activity. Without being bound by theory, the sequence of the invention may be required for appropriate folding of the active heparanase molecule which is essential for its catalytic activity, or alternatively, may be involved with the substrate recognition. As also indicated in the background of the invention, it should be noted that the 50 Kd subunit of heparanase is a cleavage product of the heparanase precursor.

As used herein in the specification and in the claims section below, the phrase "heparanase catalytic activity" or its equivalent "heparanase activity" refers to an animal endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination. Heparanase activity which is inhibited or neutralized according to the present invention can be of either recombinant or natural heparanase. Such activity is disclosed, for example, in U.S. Pat. No. 6,177,545 and U.S. Pat. No. 6,190, 875, which are incorporated by reference as if fully set forth herein.

As used herein in the specification and in the claims section below, the term N-terminus region refers to a continuous sequence involving amino acids derived from any location or locations along the 100 N'-terminal amino acids of heparanase.

In one preferred embodiment, the amino acid sequence of the invention comprises amino acid residues $Lys^{158}$ to $Asp^{171}$ of human heparanase or any functionally equivalent fragment, derivative, and variant thereof. It should be appreciated that as used herein in the specification and in the claim section below, the amino acid locations ($Lys^{158}$ to $Asp^{171}$) refers to the amino acid sequence of the human heparanase as denoted by the GenBank Accession No. AF144325.

By "functional fragments" is meant "fragments", "variants", "analogs" or "derivatives" of the molecule. A "fragment" of a molecule, such as any of the amino acid sequence of the 50 Kd subunit of heparanase used by the present invention is meant to refer to any amino acid subset of the molecule comprising the N-terminal region, and preferably, residues Lys$^{158}$ to Asp$^{171}$. A "variant" of such molecule is meant to refer to a naturally occurring molecule substantially similar to either the entire molecule or a fragment thereof. An "analog" of a molecule is a homologous molecule from the same species or from different species. By "functional" is meant having same biological function, for example, required for heparanase catalytic activity.

In another specifically preferred embodiment, the amino acid sequence of the invention comprises the amino acid sequence of any one of SEQ ID NO: 1 and SEQ ID NO: 2 and any functionally equivalent fragment, derivative, and variant thereof.

More specifically, the amino acid sequence of the invention has the amino acid sequence as denoted by SEQ ID NO: 1.

According to another alternative embodiment, the amino acid sequence of the invention has the amino acid sequence as denoted by SEQ ID NO: 2.

In a second aspect, the invention relates to an isolated and purified peptide comprising an amino acid sequence derived from the N-terminus region of the 50 Kd subunit of heparanase. The peptide of the invention is capable of competing with the corresponding sequence within the heparanase molecule and thereby inhibiting heparanase catalytic activity.

As used herein in the specification and in the claims section below, the term "inhibit" and its derivatives refers to suppress or restrain from free expression of activity. According to a preferred embodiment of the present invention at least about 60-70%, preferably, at least about, 70-80%, more preferably, at least about 80-90% of the heparanase activity is abolished by the peptide of the invention or the substance and the antibody of the invention described hereinafter. Without being bound by theory, the peptide of the invention may compete with the corresponding sequence within the native 50 Kd subunit for binding to a substrate.

According to one embodiment, the peptide of the invention comprises the amino acid residues Lys$^{158}$ to Asp$^{171}$ of human heparanase or any functionally equivalent fragment, derivative, and variant thereof.

Preferably, the peptide of the invention comprises the amino acid sequence as denoted by any one of SEQ ID NO: 1 and SEQ ID NO: 2 or any functionally equivalent fragment, derivative, and variant thereof.

According to one particular embodiment, the peptide of the invention has the amino acid sequence KKFKNSTYSRSSVD as also denoted by SEQ ID NO: 1 or any derivative thereof.

In yet another particular embodiment, the peptide of the invention has the amino acid sequence KKFKNSTYSRSSVDC as denoted by SEQ ID NO: 2 or any derivative thereof.

The terms derivatives and functional derivatives as used herein mean peptides comprising the amino acid sequence of any one of SEQ ID NO: 1 and 2, with any insertions, deletions, substitutions and modifications to the peptide that do not interfere with the peptides ability to inhibit heparanase catalytic activity (hereafter referred to as "derivative/s"). A derivative should maintain a minimal homology to said amino acid sequence, e.g. even less than 30%. It should be appreciated that the term "insertions" as used herein is meant any addition of amino acid residues to the peptides of the invention, between 1 to 50 amino acid residues, preferably, between 20 to 1 amino acid residues and most preferably, between 1 to 10 amino acid residues. Particular example is the addition of a cysteine residue to the sequence of SEQ ID NO: 1, creating a peptide of SEQ ID NO: 2.

The lack of structure of linear peptides renders them vulnerable to proteases in human serum and acts to reduce their affinity for target sites, because only few of the possible conformations may be active. Therefore, it is desirable to optimize the peptide structure, for example by creating different derivatives of the various peptides of the invention.

In order to improve peptide structure, the peptides of the invention can be coupled through their N-terminus to a laurylcysteine (LC) residue and/or through their C-terminus to a cysteine (C) residue, or to other residue/s suitable for linking the peptide to adjuvant/s for immunization, as will be described in more detail hereafter.

The peptides of the invention, as well as derivatives thereof may all be positively charged, negatively charged or neutral and may be in the form of a dimer, a multimer or in a constrained conformation. A constrained conformation can be attained by internal bridges, short-range cyclizations, extension or other chemical modification.

Further, the peptides of the invention may be extended at the N-terminus and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. One example for a synthetic amino acid residue is D-alanine.

An additional and preferred example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond.

Another example may be the incorporation of an N-terminal lysyl-palmitoyl tail, the lysine serving as linker and the palmitic acid as a hydrophobic anchor.

In addition, the peptides may be extended by aromatic amino acid residue/s, which may be naturally occurring or synthetic amino acid residue/s. A preferred aromatic amino acid residue may be tryptophan. Alternatively, the peptides can be extended at the N-terminus and/or C-terminus thereof with amino acids present in corresponding positions of the amino acid sequence of the naturally occurring N-terminus region of the 50 Kd subunit of heparanase.

Nonetheless, according to the invention, the peptides of the invention may be extended at the N-terminus and/or C-terminus thereof with various identical or different organic moieties which are not naturally occurring or synthetic amino acids. As an example for such extension, the peptide may be extended at the N-terminus and/or C-terminus thereof with an N-acetyl group.

For every single peptide sequence used by the invention and disclosed herein, this invention includes the corresponding retro-inverso sequence wherein the direction of the peptide chain has been inverted and wherein all the amino acids belong to the D-series.

It is to be appreciated that the present invention also includes longer peptides in which part or all of the basic Lys$^{158}$ to Asp$^{171}$ amino acid residues which comprises the amino acid sequence as denoted by SEQ ID NO: 1, or in which the basic peptidic sequence of the peptide of the invention SEQ ID NOs: 1 or 2 is repeated from about 2 to about 100 times.

It should be noted that the amino acid location (residues Lys$^{158}$ to Asp$^{171}$ of heparanase) refers to the amino acid sequence of the human heparanase as denoted by the Genbank Accession No. AF144325.

A further aspect of the invention relates to a composition for the inhibition of heparanase glycosidase catalytic activity, comprising as an active ingredient an isolated and purified peptide, which comprises an amino acid sequence derived from the N-terminus region of the 50 Kd subunit of heparanase. This composition optionally further comprising a pharmaceutically acceptable carrier, diluent, excipient and/or additive.

In a particular embodiment, the composition of the invention comprises as an active ingredient the amino acid residues Lys$^{158}$ to Asp$^{171}$ of human heparanase or any functionally equivalent fragment, derivative, and variant thereof.

Preferably, the peptide comprised within such composition has the amino acid sequence as denoted by SEQ ID NO: 1 or any derivative thereof. Alternatively, this peptide has the amino acid sequence as denoted by SEQ ID NO: 2 or any derivative thereof.

The invention further provides for a pharmaceutical composition for the treatment or the inhibition of a process or a pathologic disorder associated with heparanase catalytic activity. Such composition may comprise as an active ingredient, an isolated and purified peptide comprising an amino acid sequence derived from the N-terminus region of the 50 Kd subunit of heparanase, in an amount sufficient for the inhibition of heparanase glycosidase catalytic activity. It should be noted that this composition optionally further comprises a pharmaceutically acceptable carrier, diluent, excipient and/or additive.

As used herein in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

As used herein in the specification and in the claims section below, the phrase "associated with heparanase catalytic activity" refers to conditions which at least partly depend on the catalytic activity of heparanase. It is being understood that the catalytic activity of heparanase under many such conditions can be normal, yet inhibition thereof in such conditions will result in improvement of the affected individual.

It should be further noted that disorders or the condition can be related to altered function of a HSPG associated biological effector molecule, such as, but not limited to, growth factors, chemokines, cytokines and degradative enzymes. The condition can be, or involve, angiogenesis, tumor cell proliferation, invasion of circulating tumor cells, metastases, inflammatory disorders, autoimmune conditions and/or a kidney disorder.

According to a particular embodiment, the peptide comprised within the pharmaceutical composition of the invention comprises the amino acid residues Lys$^{158}$ to Asp$^{171}$ of human heparanase or any functionally equivalent fragment, derivative, and variant thereof. Preferably, such peptide has the amino acid sequence as denoted by SEQ ID NO: 1, SEQ ID NO: 2 or any derivative thereof.

The heparanase inhibitors (e.g., the peptides described herein, as well as the specific substances and the specific antibody, which will be described hereinafter) of the present invention may be used for the treatment of diseases and disorders caused by or associated with heparanase catalytic activity such as, but not limited to, cancer, inflammatory disorders, autoimmune diseases or a kidney disorder.

Involvement in tumor angiogenesis of heparanase has been correlated with the ability to release bFGF (FGF-2) and other growth factors from its storage within the ECM (extracellular matrix). These growth factors provide a mechanism for induction of neovascularization in normal and pathological situations.

Heparanase may thus facilitate not only tumor cell invasion and metastasis but also tumor angiogenesis, both critical steps in tumor progression.

It is to be therefore understood that the compositions of the invention are useful for treating or inhibiting tumors at all stages, namely tumor formation, primary tumors, tumor progression or tumor metastasis.

Thus, in one embodiment of the present invention, the compositions of the invention can be used for inhibition of angiogenesis, and are thus useful for the treatment of diseases and disorders associated with angiogenesis or neovascularization such as, but not limited to, tumor angiogenesis, opthalmologic disorders such as diabetic retinopathy and macular degeneration, particularly age-related macular degeneration, and reperfusion of gastric ulcer.

As used herein to describe the present invention, "malignant proliferative disorder" "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the composition as well as the methods of the present invention may be used in the treatment of non-solid and solid tumors, for example, carcinoma, melanoma, leukemia, and lymphoma.

Therefore, according to a preferred embodiment, the peptide of the invention or a composition comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

The peptides of the invention or any compositions thereof, as well as any other heparanase inhibitors of the invention (e.g., a substance which binds to the sequence of residues Lys$^{158}$ to Asp$^{171}$, or the specific antibody, preferably #733 of the invention) may be also useful for inhibiting or treating other cell proliferative diseases or disorders such as psoriasis, hypertrophic scars, acne and sclerosis/scleroderma, and for inhibition or treatment of other diseases or disorders such as polyps, multiple exostosis, hereditary exostosis, retrolental fibroplasia, hemangioma, and arteriovenous malformation.

Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity [Vladavsky, I. et al., Invasion &

Metastasis 12, 112-127 (1992)]. The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparan sulfate degrading enzymes released by platelets and macrophages are likely to be present in atherosclerotic lesions [Campbell, K. H. et al. Exp. Cell Res. 200, 156-167 (1992)]. Treatment of experimental animals with heparanase alternative substrates (e.g., non-anticoagulant species of low molecular weight heparin) markedly reduced the incidence of experimental autoimmune encephalomyelitis (EAE), adjuvant arthritis and graft rejection [Vlodavsky (1992) ibid.; Lider, O. et al., J. Clin. Invest. 83:752-756 (1989)] in experimental animals, indicating that heparanase inhibitors may be applied to inhibit autoimmune and inflammatory diseases.

Therefore, in a further embodiment, the compositions of the invention may be useful for treatment of or amelioration of inflammatory symptoms in any disease, condition or disorder where immune and/or inflammation suppression is beneficial such as, but not limited to, treatment of or amelioration of inflammatory symptoms in the joints, musculoskeletal and connective tissue disorders, or of inflammatory symptoms associated with hypersensitivity, allergic reactions, asthma, atherosclerosis, otitis and other otorhinolaryngological diseases, dermatitis and other skin diseases, posterior and anterior uveitis, conjunctivitis, optic neuritis, scleritis and other immune and/or inflammatory ophthalmic diseases.

In another preferred embodiment, the compositions of the invention are useful for treatment of or amelioration of an autoimmune disease such as, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjbgren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pernphigoid, dennatitis herpetiformis, insulin dependent diabetes, inflammatory bowel disease, ulcerative colitis and Crohn's disease.

Still further, heparanase has been proposed to be involved in the pathogenesis of proteinuria by selectively degrading the negatively charged side chains of heparan sulfate proteoglycans within the glomerular basement membrane. A loss of negatively charged heparan sulfate proteoglycans may result in alteration of the permselective properties of the glomerular basement membrane, loss of glomerular epithelial and endothelial cell anchor points, and liberation of growth factors and potentially leading to different kidney disorders, such as, passive Heymann nephritis (PHN), and puromycin aminonucleoside nephrosis (PAN). As described by Levidiotis, V. et al. [Levidiotis, V. et al., J. Am. Soc. Nephrol. 15, 68-78 (2004)], a polyclonal antibody against heparanase, significantly reduced proteinuria without affecting the histologic appearance of glomeruli and the immune mechanisms, which give rise to PHN, and therefore, inhibition of heparanase may be used to reduce proteinuria.

Therefore, in another preferred embodiment, the compositions of the invention are useful for treatment of or amelioration of any kidney disorder.

The composition of the invention may comprise the active substance in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (IP), intravenous (IV) and intradermal administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

More specifically, said antibody, peptide or any substance or a composition comprising the same, having heparanase inhibitory activity, may be administered by a route selected from oral, intravenous, parenteral, transdermal, subcutaneous, intravaginal, intranasal, mucosal, sublingual, topical and rectal administration and any combinations thereof.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

It should be noted that these are applicable for any composition described by the present invention.

In a further aspect, the invention provides the use of an isolated and purified peptide comprising an amino acid sequence derived from the N-terminus region of the 50 Kd subunit of heparanase, for the inhibition of heparanase glycosidase catalytic activity.

Still further, the invention provides for the use of an isolated and purified peptide comprising an amino acid sequence derived from the N-terminus region of the 50 Kd subunit of heparanase, in the preparation of a composition for the inhibition of heparanase glycosidase catalytic activity.

According to a specifically preferred embodiment, the peptide used is the peptide defined by the invention.

The invention further relates to the use of an isolated and purified peptide comprising an amino acid sequence derived from the N-terminus region of the 50 Kd subunit of heparanase, in the preparation of a pharmaceutical composition for the treatment or the inhibition of a process or a pathologic disorder associated with heparanase glycosidase catalytic activity. Such composition optionally further comprising a pharmaceutically acceptable carrier, diluent, excipient and/or additive. Preferably, the peptide used is the peptide defined by the present invention.

According to a preferred embodiment, the use of such peptide according to the invention is for the preparation of a pharmaceutical composition for the inhibition or treatment of a process associated with heparanase catalytic activity, such as, angiogenesis, tumor formation, tumor progression and tumor metastasis. In another embodiment, the use is for a pathologic disorder such as a malignant proliferative disorder, for example, solid and non-solid tumor selected from the group consisting of carcinoma, sarcoma, melanoma, leukemia and lymphoma.

The use according to another embodiment may be for the treatment of an inflammatory disorder, autoimmune disorder and a kidney disorder.

The invention further provides for a method for the inhibition of heparanase glycosidase catalytic activity comprising the step of in vivo or in vitro contacting heparanase under suitable conditions, with an inhibitory effective amount of an isolated and purified peptide comprising an amino acid sequence derived from the N-terminus region of the 50 Kd subunit of heparanase, or with a composition comprising the same. It should be noted that the heparanase used by the method of the invention may be provided as a purified recombinant heparanase protein, a fusion heparanase protein, a nucleic acid construct encoding for heparanase, a host cell expressing said construct, a cell, a cell line and a tissue endogenously expressing the active form of heparanase, or any lysates thereof.

Still further, the invention provides a method for the inhibition of heparanase glycosidase catalytic activity in a subject in need thereof. This method comprises the step of administering to the subject an inhibitory effective amount of an isolated and purified peptide comprising an amino acid sequence derived from the N-terminus region of the 50 Kd subunit of heparanase, or of a composition comprising the same.

In another embodiment, the invention relates to a method for the inhibition or the treatment of a process or a pathologic disorder associated with heparanase glycosidase catalytic activity. Such method comprises the step of administering to a subject in need thereof a therapeutically effective amount of an isolated and purified peptide comprising an amino acid sequence derived from the N-terminus region of the 50 Kd subunit of heparanase, or of a composition comprising the same.

According to a specific embodiment, the method of the invention is intended for the inhibition or the treatment of a process associated with heparanase catalytic activity such as, angiogenesis, tumor formation, tumor progression and tumor metastasis, a malignant proliferative disorder such as solid and non-solid tumor selected from the group consisting of carcinoma, sarcoma, melanoma, leukemia and lymphoma and an inflammatory disorder, an autoimmune disorder or a kidney disorder.

The therapeutically 'effective amount' for purposes herein is that determined by such considerations as are known in the art. The amount must be sufficient to inhibit the correct folding of the heparanase molecule and thereby to inhibit heparanase catalytic activity.

According to a specifically preferred embodiment, the peptide used for these methods is the peptide of the invention.

The pharmaceutical composition used by the method of the invention can be prepared in dosage units forms and may be prepared by any of the methods well-known in the art of pharmacy. In addition, the pharmaceutical composition may further comprise pharmaceutically acceptable additives such as pharmaceutical acceptable carrier, excipient or stabilizer, and optionally other therapeutic constituents. Naturally, the acceptable carriers, excipients or stabilizers are non-toxic to recipients at the dosages and concentrations employed.

The magnitude of therapeutic dose of the composition of the invention will of course vary with the group of patients (age, sex, etc.), the nature of the condition to be treated and with the route administration and will be determined by the attending physician.

Although the method of the invention is particularly intended for the treatment of disorders associated with heparanase catalytic activity in humans, other mammals are included. By way of non-limiting examples, mammalian subjects include monkeys, equines, cattle, canines, felines, rodents such as mice and rats, and pigs.

The pharmaceutical composition of the invention can be administered and dosed in accordance with good medical practice. Administration may be carried out in various ways, including intravenous, intramuscular or subcutaneous injection. However, other methods of administration such as intranasal administration are also possible.

This should be applicable for any method disclosed by the present application.

In another aspect, the invention relates to a method of screening for a test substance which specifically binds to an amino acid sequence derived from the N-terminus region of the 50 Kd subunit of heparanase and is capable of inhibiting heparanase glycosidase catalytic activity. The screening method of the invention comprises the steps of: (a) obtaining a test substances which bind to the 50 Kd subunit of heparanase; (b) selecting from the 50 Kd subunit of heparanase-binding substances obtained in step (a), a candidate substance that specifically binds to a sequence comprising amino acid residues $Lys^{158}$ to $Asp^{171}$ of heparanase; and (c) evaluating the candidate substance obtained in step (b) by determining its inhibitory effect on the glycosidase catalytic activity of heparanase.

Key to the application of high-throughput screening for high-affinity binding of substances, preferably, antibodies or a peptide, is the development of a sensitive and convenient screening assay.

Development of a robust screening assay for substances, through their affinity for the 50 Kd subunit of heparanase, will be the first step in said screening method.

In a preferred embodiment, the candidate substance utilized by the screening method of the invention may be obtained by the steps of: (a) providing a mixture comprising the 50 Kd subunit of heparanase or any fragment thereof; (b) contacting said mixture with said test substance under suitable conditions for said binding; and (c) determining the effect of the test substance on an end-point indication, whereby modulation of said end point is indicative of binding of the 50 Kd subunit of heparanase to said test substance.

According to a specifically preferred embodiment, the end point indication may be the binding of an antibody specific for the 50 Kd subunit of heparanase, to the 50 Kd subunit of heparanase. Such binding leads to a visually detectable signal.

More particularly, each candidate substance, or preferably, peptide, may be placed in a well and direct binding of the 50 Kd subunit of heparanase is detected preferably by commercial tagged antibody against heparanase or by any of the antibodies mentioned in Experimental procedures hereinafter. Conditions for effective binding of the 50 Kd subunit to the peptide on the plate may be first optimized using a specific antibody, for example, #733 of the invention. This involves study of pH, salt and buffer composition, carrier proteins such as BSA. This robust screening yields substances, preferably peptides that bind to 50 Kd subunit of heparanase. Substances that bind 50 Kd subunit of heparanase are pooled and then assayed as described below.

In the second step of the screening method of the invention, the candidate substances which bind the 50 Kd subunit of heparanase (that were preferably obtained as described above), may be further selected for their ability to specifically bind to the 50 Kd subunit molecule at the N-terminal region comprising residues $Lys^{158}$ to $Asp^{171}$ of heparanase. Such selected substances will desirably be capable of preventing the correct folding of the heparanase molecule and thereby inhibit heparanase catalytic activity, or alternatively may interfere the binding of heparanase to its substrate. According to this embodiment, selection of such substances may be performed by the steps of: (a) providing a mixture comprising the 50 Kd subunit of heparanase or any derivatives homologous, variants and fragment thereof; (b) contacting said mixture with said test substance under suitable conditions; and (c) determining the effect of the test substance on an end-point indication, whereby modulation of said end point is indicative of binding of the test substance to the sequence comprising amino acid residues $Lys^{158}$ to $Asp^{171}$ of the 50 Kd subunit of human heparanase.

According to a preferred embodiment, the mixture used by the method of the invention may comprise: (a) the 50 Kd subunit of heparanase or any fragment thereof; (b) an interfering molecule selected from a peptide comprising amino acid residues $Lys^{158}$ to $Asp^{171}$ of human heparanase and an antibody specific for a sequence comprising amino acid residues $Lys^{158}$ to $Asp^{171}$ of human heparanase; and (c) optionally solutions, buffers and/or compounds which provide suitable conditions for interaction of said interfering molecule with the 50 Kd subunit of heparanase or with the candidate substance and for the detection of an end-point indication for the interaction of said candidate substance with the 50 Kd subunit of heparanase.

More particularly, each candidate substance, or preferably, peptide, may be bound to a solid support (for example, a well of a microplate) and direct binding of the 50 Kd subunit of heparanase to the tested substance may be monitored by adding an anti-50 kd antibody (preferably, this antibody should be directed to the C' terminus of the 50 kd subunit). Thus, addition of an interfering molecule to such competition assay may lead to decrease in binding of the 50 kd subunit to the tested substance on the plate. For example, where the interfering molecule is a specific peptide (preferably, a peptide comprising amino acid residues $Lys^{158}$ to $Asp^{171}$), such peptide may bind to the test substance attached to the plate. Such binding competes with the 50 Kd subunit and therefore leads to decrease in the end point. Alternatively, an anti-$lys^{158}$ to $Asp^{171}$ antibody (antibody #733 of the invention, for example), may be used as an interfering molecule. This antibody will bind the 50 kd in the reaction mixture provided and thereby block the binding of the 50 kd to the substance on plate via this site.

As indicated above, the end point indication in this assay may be the binding of an anti-50 Kd subunit of heparanase antibody to the 50 Kd subunit of heparanase, which binding leads to a visually detectable signal.

Inhibition in said end point is indicative of inhibition of the direct binding of the test substance to a sequence comprising amino acid residues $Lys^{158}$ to $Asp^{171}$ of human heparanase within the 50 KD subunit of heparanase. Only specific binding may be specifically competed by the binding of the interfering molecules, for example, an antibody directed for a sequence comprising amino acid residues $Lys^{158}$ to $Asp^{171}$ of human heparanase to said site within the 50 KD subunit of heparanase, or by the binding of the interfering peptide comprising amino acid residues $Lys^{158}$ to $Asp^{171}$ of human heparanase to the tested substance.

An alternative approach is to use labeled, preferably, biotinylated antibody specific for SEQ ID NO: 1 or 2 (preferably, antibody #733, of the present invention) as the interfering molecule and assay for the ability of the test substance to displace labeled antibody from binding to the 50 Kd subunit of heparanase on the plate.

In yet another alternative, such selection step of the screening method may be performed for example, where the 50 Kd subunit of heparanase is bound onto the wells of a microplate. Then, each well is incubated with a limiting amount of an antibody specific for the sequence of residues $Lys^{158}$ to $Asp^{171}$ of the 50 Kd subunit of heparanase, as the interfering molecule, in the presence of the test substance. Supernatant is collected from each well. Unbound Ab is detected in the supernatant by secondary antibody ELISA. Should the substance bind tightly to the 50 Kd subunit of heparanase a sequence comprising residues $Lys^{158}$ to $Asp^{171}$, it will compete in the binding of antibody, preferably, #733, to the 50 Kd subunit of heparanase and release free Ab that can be detected over a zero background, rendering the assay sensitive. Candidate substance or peptides binding outside the N-terminal region of the 50 Kd subunit of heparanase, will be eliminated by this approach.

According to one alternative embodiment, the mixture utilized by the method of the invention may be a cell-free mixture. Such mixture comprises the 50 Kd subunit of heparanase or any functional fragment thereof (preferably, comprising residues $Lys^{158}$ to $Asp^{171}$ of heparanase), that may be provided as any one of a purified recombinant protein, a fusion protein and a cell lysate or membrane preparation of a transformed host cell expressing the said 50 Kd subunit.

A particular alternative example for such selection may be based on the use of a variant of the 50 Kd subunit, which is preferably a deletion mutant. More preferably, the deletion mutant is the 50 Kd subunit of heparanase devoid of residues $Lys^{158}$ to $Asp^{171}$.

Such mutated 50 Kd subunit of heparanase may be provided as a purified recombinant protein, a cell lysate or membrane preparation of a transformed host cell expressing said mutated 50 Kd subunit.

Accordingly, comparative binding of the test substance to a mutated and wild type molecule will distinguish between test substances which bind the particular sequence of the invention, and those which bind other regions of the 50 Kd subunit. Thus, the end point indication may be the binding of an anti-50 Kd subunit of heparanase antibody to the mutated 50 Kd subunit of heparanase, which binding leads to a visually detectable signal. Inhibition of such end point indicates that the test substance does not bind to the mutated 50 Kd subunit of heparanase and therefore specifically binds to a sequence comprising residues $Lys^{158}$ to $Asp^{171}$ of heparanase.

Alternatively, the mixture utilized for the selection step by the method of the invention may be a cell mixture. Preferably, the cell mixture may be a transfected cell culture.

In a particular preferred embodiment, the transfected cells are cells transfected with an expression vector comprising a nucleic acid sequence coding for the 50 Kd subunit of heparanase or any fragment thereof (preferably, any fragment comprising amino acid residues $Lys^{158}$ to $Asp^{171}$ of heparanase).

According to a preferred embodiment, the transfected cells are cells transfected with any one of an expression vector comprising a nucleic acid sequence coding for the 50 Kd subunit of heparanase or any fragment thereof and an expression vector comprising a nucleic acid sequence coding for the mutated 50 Kd subunit of heparanase devoid of residues $Lys^{158}$ to $Asp^{171}$ of heparanase.

In this particular embodiment, each candidate substance obtained by the method of the invention, is labeled and contacted with the cells. Accordingly, the binding of the labeled substance to cells transfected with a nucleic acid sequence coding for the 50 Kd subunit of heparanase (the wild type subunit) is determined and compared to the binding of the same substance to cells transfected with an expression vector comprising a nucleic acid sequence coding for the mutated 50 Kd subunit of heparanase (devoid of residues $Lys^{158}$ to $Asp^{171}$ of human heparanase).

Alternatively, each candidate substance, for example a peptide, is placed in a well and the well is then blocked with BSA or fetal calf serum. Comparative binding of transfected cells that express for example, the chimeric membranal 50 Kd-PDGF-R molecule described in Experimental procedures hereinafter and cells expressing similar 50 Kd-PDGF-R chimera devoid of residues $Lys^{158}$ to $Asp^{171}$ of heparanase, on their cell surface is scored visually, or by anti-50 Kd subunit ELISA. Alternatively, cell membranes or lysates prepared from the transfected cells may be used and binding may be detected using anti-50 Kd antibody. Positive candidate substances are then re-examined in the presence of the interfering molecules, e.g. the peptide of the invention or antibody specific for a sequence comprising residues $Lys^{158}$ to $Asp^{171}$ sequence (SEQ ID NO: 1 or 2), preferably #733, as competitor.

The candidate substance obtained and selected by the screening method of the invention, may be any one of protein based, carbohydrates based, lipid based, natural organic based, synthetically derived organic based, inorganic based, and peptidomimetics based substances.

Such substance may be for example a product of positional scanning of combinatorial libraries of peptides, libraries of cyclic peptidomimetics, and random or dedicated phage display libraries.

Where the candidate substance obtained and selected by the screening method of the invention, is a peptide, combinatorial phage libraries may be used to screen for a substance which specifically binds amino acid sequence comprising residues $Lys^{158}$ to $Asp^{171}$ of heparanase.

Panning may be performed in two stages, in the first stage, bound phage are eluted from microplate-bound 50 Kd subunit of heparanase using elution for example, at pH 2.2. This will select all phages that bind the 50 Kd subunit of heparanase, including binders to domains in the 50 Kd subunit that do not include residues $Lys^{158}$ to $Asp^{171}$. Thus, in the second stage, phage selected as above are bound to 50 Kd subunit of heparanase and eluted specifically with an excess of free peptide of the invention which comprises the amino acid sequence of SEQ ID NO: 1 or 2. Bound phages are eluted and subjected to 2-3 further cycles of panning. Then, direct binding of phage to immobilized 50 Kd subunit of heparanase or to any fragment thereof comprising the $Lys^{158}$ to $Asp^{171}$ sequence, may be detected by phage ELISA, scoring for M13 on the plate. Positive phage clones are amplified and sequenced, before synthesis of the peptides in linear form.

In an alternative panning strategy, the 50 Kd subunit of heparanase cDNA transiently overexpressed in transfected cells as described above may be used. Cells may be immobilized on the plate. Panning of phage-displayed peptides may be done first on cells transfected with the mutated 50 Kd subunit of heparanase, which devoid of residues $Lys^{158}$ to $Asp^{171}$, to eliminate nonspecific binders, and then on transfected cells that overexpress the 50 Kd subunit of heparanase (or cells that overexpress a fragment of the 50 Kd subunit comprising the sequence of residues $Lys^{158}$ to $Asp^{171}$) on their cell surface. Alternatively, whole cell membrane preparations may be substituted for cells. 50 Kd subunit-bound phage are eluted with an excess of free interfering molecules, such as the peptide of the invention having the amino acid sequence of any one of SEQ ID NO: 1 or 2, or an antibody specific for this sequence (for example, the #733 antibody of the invention).

Peptides selected from each of the random and the dedicated libraries may be then evaluated for their ability to inhibit heparanase catalytic activity, according to the evaluation step of the screening method of the invention, described hereafter.

As used herein, screening of a combinatorial library, is an approach where a large library of chemically diversed molecules (such as peptides, as described above) are screened for the desired biological activity, for example, specific binding to a sequence comprising amino acid residues 158 to 171 of heparanase, and thereby inhibition of heparanase catalytic activity. This approach has become an effective and hence important tool for discovery of new drugs, and is based on "combinatorial" synthesis of a diverse set of molecules in which several components predicted to be associated with the desired biological activity are systematically varied. The advantage of a combinatorial library over the alternative use of natural extracts for screening for desired biologically active compounds is that all the components comprising the library are known in advance.

In combinatorial screening, the number of hits discovered is proportional to the number of molecules tested. This is true even when knowledge concerning the target is unavailable. The large number of compounds, which may reach thousands of compounds tested per day, can only be screened, provided that a suitable assay involving a high throughput screening technique, in which laboratory automation and robotics may be applied, exists.

According to a particular embodiment, the test substance may be an antibody specific for a sequence comprising amino acid residues $Lys^{158}$ to $Asp^{171}$ of human heparanase.

The third step of the screening method involves evaluation of the selected test substance ability of to inhibit heparanase glycosidase catalytic activity, which evaluating method comprises the steps of: (a) providing a test system comprising an active heparanase molecule or any functional fragments thereof, and a heparanase substrate; (b) contacting said system with a candidate substance obtained and selected by the method of the invention, under conditions suitable for heparanase catalytic activity; and (c) determining the effect of the candidate substance on an end-point indication as compared to a control. Such effect is indicative of the capability of the candidate substance to inhibit heparanase catalytic activity.

According to one embodiment, the test system may be any one of cell free mixture and in-vitro/ex-vivo cell culture.

According to a specifically preferred embodiment, the test system may be a cell-free mixture. Accordingly, is such system heparanase may be provided as any one of a purified recombinant protein, and a cell lysate or membrane preparation of a transformed host cell.

In an alternative embodiment, the test system may be an in-vitro/ex-vivo cell culture comprising an endogenously expressed heparanase or exogenously expressed heparanase.

It should be noted that any heparanase substrate may be used for evaluation of the test substance. Suitable substrates may be for example, extracellular matrix (ECM) and any portion thereof, macromolecules associated with said ECM, ECM-derived soluble heparan sulfate proteoglycans, heparan sulfate and heparin.

The end point indication may be therefore, the determination of degradation products of such heparanase substrate by a suitable means. More specifically, any known heparanase catalytic activity assay.

Several methods for determining heparanase catalytic activity have been developed over the years. Most of the different methods are based on radiolabeling of a substrate (either in vitro or metabolically), and analysis of its degradation products released due to heparanase catalytic activity. Thus, most heparanase assays also require extensive degradation of the radiolabeled HS (or matrix-derived HSPG) substrate to allow separation of the degraded product from the substrate by gel filtration. Solid-phase heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is herein incorporated in its entirety.

One example for heparanase catalytic activity assay, is an assay developed by Freeman and Parish [Freeman, C. & Parish, C. R: Biochem. J. 325; 229-237 (1997)] the products are separated from the substrate by binding to chicken histidine-rich glycoprotein (cHRG) sepharose. In this method only the lowest molecular weight products that lose the ability to bind to cHRG sepharose are detectable, while other, longer, products bind to the column with the substrate and are therefore excluded.

Another example for heparanase assay, the quantitative assay disclosed in U.S. Pat. No. 6,190,875, is based on detection of newly formed reducing ends produced due to cleavage of polysaccharides, such as, heparin or heparan sulfate by heparanase. This assay detects every single cleavage.

Still further, there are also some non-radioactive assays available for heparanase. The most used assay for heparanase involves measuring the optical density (at 230 nm) of unsaturated uronic acids formed during degradation of heparin. Another color-based assay for measuring heparanase activity utilizes heparin's ability to interfere with color development during the interaction of protein with the dye Coomassie brilliant blue [Khan, M. Y. and Newman, S. A. Anal. Biochem. 196, 373-6 (1991)]. In yet another assay disclosed in U.S. Pat. No. 6,656,699, a composition comprising biotin-HS is mixed with a sample (such as a tumor sample, bodily fluid, or other fluid suspected of having heparanase activity), to form a reaction mixture. This sample may be pretreated to remove contaminating or reactive substances such as endogenous biotin. After incubation, an aliquot or portion of the reaction mixture is removed and placed in a biotin-binding plate. After washing with buffers, a Streptavidin-enzyme conjugate is added to the biotin-binding plate. Reagents for the enzyme are added to form a detectable color product. For example, a decrease in color formation, from a known standard, indicates there was heparanase activity in the sample.

Preferably, heparanase catalytic activity may be determined for the evaluation step, as described in Experimental procedures hereinafter.

As a control in these assays, determination of the catalytic activity of heparanase in the absence of the candidate substance should be performed.

The present invention further provides a method of preparing a therapeutic composition for the treatment of a process or a pathologic disorder associated with heparanase glycosidase catalytic activity in a mammalian subject. Such method comprises the steps of: (a) identifying a substance that is capable of specifically inhibiting heparanase glycosidase catalytic activity by binding to an amino acid sequence derived from the N-terminus region of the 50 Kd subunit of heparanase; and (b) admixing said candidate substance with at least one of a pharmaceutically acceptable carrier, diluent, excipient and additive.

According to a specifically preferred embodiment, the substance used by such method may be identified by the screening method of the invention disclosed herein before.

In yet another aspect, the invention relates to a substance which specifically binds to an amino acid sequence derived from the N-terminus region of the 50 Kd subunit of heparanase and is capable of inhibiting heparanase glycosidase catalytic activity. Preferably, this substance binds an amino acid sequence which comprises the amino acid residues $Lys^{158}$ to $Asp^{171}$ of human heparanase or any functionally equivalent fragment, derivative and variant thereof, most preferably, the amino acid sequence defined by the invention.

According to a specifically preferred embodiment, the substance of the invention is obtained by the screening method of the invention.

The invention further provides a composition for the inhibition of heparanase glycosidase catalytic activity, comprising as an active ingredient a substance which specifically binds to an amino acid sequence derived from the N-terminus region of the 50 Kd subunit of heparanase and is capable of inhibiting heparanase glycosidase catalytic activity, said composition optionally further comprising a pharmaceutically acceptable carrier, diluent, excipient and/or additive.

Preferably, the substance used for such composition is the substance as defined by the invention.

Inhibition of heparanase activity by such substance may thus, for example, prevent angiogenesis caused due to the activation of bFGF, and allow inhibition of cell proliferation, such as tumor cell proliferation.

Still further, inhibition of heparanase activity may also be used to inhibit degradation of the basement membrane, which allows invasion of circulating tumor cells, and thus prevent metastasis.

In a similar mechanism, neutralization of heparanase activity may prevent from activated cells of the immune system to leave circulation and thus inhibit elicitation of both inflammatory disorders and autoimmune responses.

Thus, the invention relates to a pharmaceutical composition for the treatment or the inhibition of a process or a pathologic disorder associated with heparanase catalytic activity. Such composition comprises as an active ingredient, a substance which specifically binds to an amino acid sequence derived from the N-terminus region of the 50 Kd subunit of heparanase and is capable of inhibiting heparanase glycosidase catalytic activity, in an amount sufficient for the inhibition of heparanase glycosidase catalytic activity. The composition of the invention optionally further comprises a pharmaceutically acceptable carrier, diluent, excipient and/or additive. Preferably, the substance used for such pharmaceutical composition is the substance defined by the invention.

The pharmaceutical composition of the invention is applicable for the treatment of process and pathologic disorders associated with heparanase catalytic activity, for example, a process such as angiogenesis, tumor formation, tumor progression and tumor metastasis, and a malignant proliferative disorder such as solid and non-solid tumor selected from the group consisting of carcinoma, sarcoma, melanoma, leukemia, and lymphoma. Still further, the pharmaceutical composition of the invention may be applicable for the treatment of inflammatory disorder, autoimmune disorder or a kidney disorder.

In yet another aspect, the invention relates to the use of the substance of the invention for the inhibition of heparanase glycosidase catalytic activity.

The invention further relates to the use of the substance of the invention, in the preparation of a composition for the inhibition of heparanase glycosidase catalytic activity.

According to another preferred embodiment, the invention relates to the use of the substance defined by the invention, in the preparation of a pharmaceutical composition for the treatment or the inhibition of a process or a pathologic disorder associated with heparanase glycosidase catalytic activity, said composition optionally further comprising a pharmaceutically acceptable carrier, diluent, excipient and/or additive. A process associated with heparanase catalytic activity, may be angiogenesis, tumor formation, tumor progression and tumor metastasis. A pathologic disorder may be a malignant proliferative disorder or inflammatory disorder, autoimmune disorder and a kidney disorder.

The invention further relates to method for the inhibition of heparanase glycosidase catalytic activity comprising the step of in vivo or in vitro contacting heparanase, under suitable conditions, with an inhibitory effective amount of the substance of the invention, or with a composition comprising the same.

In another embodiment, the invention relates to a method for the inhibition of heparanase glycosidase catalytic activity in a subject in need thereof comprising the step of administering to said subject an inhibitory effective amount of a substance which specifically binds to an amino acid sequence derived from the N-terminus region of the 50 Kd subunit of heparanase and is capable of inhibiting heparanase glycosidase catalytic activity, preferably, the substance of the invention, or of a composition comprising the same.

Still further, the invention relates to a method for the inhibition or the treatment of a process or a pathologic disorder associated with heparanase glycosidase catalytic activity comprising the step of administering to a subject in need thereof a therapeutically effective amount of the substance of the invention, or of a composition comprising the same.

It should be noted that such methods are applicable for a process associated with heparanase catalytic activity, for example, angiogenesis, tumor formation, tumor progression or tumor metastasis, for a malignant proliferative disorder, such as a solid or non-solid tumor selected from the group consisting of carcinoma, sarcoma, melanoma, leukemia and lymphoma, or for inflammatory disorder, autoimmune disorder and or a kidney disorder.

The pharmaceutical compositions of the invention may be administered by the methods of the invention, systemically, for example by parenteral, e.g. intravenous, intraperitoneal or intramuscular injection. In another example, the pharmaceutical composition can be introduced to a site by any suitable route including intravenous, subcutaneous, transcutaneous, topical, intramuscular, intraarticular, subconjunctival, or mucosal, e.g. oral, intranasal, or intraocular administration.

Local administration to the area in need of treatment may be achieved by, for example, local infusion during surgery, topical application, direct injection into the inflamed joint, directly onto the eye, etc.

For oral administration, the pharmaceutical preparation may be in liquid form, for example, solutions, syrups or suspensions, or in solid form as tablets, capsules and the like. For administration by inhalation, the compositions are conveniently delivered in the form of drops or aerosol sprays. For administration by injection, the formulations may be presented in unit dosage form, e.g. in ampoules or in multidose containers with an added preservative.

The compositions of the invention can also be delivered in a vesicle, for example, in liposomes. In another embodiment, the compositions can be delivered in a controlled release system.

The amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well in vivo experiments may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

As used herein, "effective amount" means an amount necessary to achieve a selected result. For example, an effective amount of the composition of the invention useful for inhibition of heparanase activity and thereby for the treatment of said pathology.

In yet another aspect, the invention relates to an antibody which specifically recognizes an amino acid sequence derived from the N-terminus region of the 50 Kd subunit of heparanase. By the term "specifically recognizes" is meant that the amino acid sequence of the invention or any fragment or derivative thereof, serves as an epitope for such antibody.

The term "epitope" as used herein is meant to refer to that portion of any molecule capable of being bound by an antibody that can also be recognized by that antibody. Epitopes or "antigenic determinants" usually consist of chemically active surface groupings of molecules such as amino acids or sugar side chains, and have specific three-dimensional structural characteristics as well as specific charge characteristics.

According to a preferred embodiment, the antibody of the invention specifically recognizes amino acid sequence comprising the amino acid residues $Lys^{158}$ to $Asp^{171}$ of human heparanase or any functionally equivalent fragment, derivative, and variant thereof, preferably, the amino acid sequence defined by the invention. More specifically, a sequence comprising the amino acid sequence of SEQ ID NO: 1.

In a specifically preferred embodiment, such antibody specifically recognizes the active form of heparanase.

In yet another specifically preferred embodiment, the antibody of the invention is capable of inhibiting heparanase glycosidase catalytic activity.

It should be appreciated that the antibody of the invention may be a polyclonal or a monoclonal antibody.

The generation of polyclonal antibodies against proteins is described in Chapter 2 of Current Protocols in Immunology, Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells.

The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described in by Kohler and Milstein, Nature 256; 495-497, (1975), and in U.S. Pat. No. 4,376,110.

The term "antibody" is meant to include intact molecules as well as fragments thereof, such as, for example, Fab and F(ab')$_2$, which are capable of binding antigen.

It will be appreciated that Fab and F(ab')$_2$ and other fragments of the antibodies are within the scope of the present invention and may be used for the compositions and the methods disclosed herein for intact antibody molecules. Such fragments are typically produced by proteolytic cleavage, using enzymes such as papain (to produce Fab fragments) or pepsin (to produce F(ab')$_2$ fragments).

For future clinical applications, where the anti-heparanase antibody is a monoclonal antibody, it may be improved, through a humanization process, to overcome the human antibody to mouse antibody response. Rapid new strategies have been developed recently for antibody humanization which may be applied for such antibody. These technologies maintain the affinity, and retain the antigen and epitope specificity of the original antibody Rader, C., et al., Proc. Natl. Acad. Sci. 95, 8910-8915 (1998); Mateo, C., et al., Immunothechnology 3, 71-81 (1997)]. A "humanized" antibody, in which, for example animal (say murine) variable regions are fused to human constant regions, or in which murine complementarity-determining regions are grafted onto a human antibody. Unlike, for example, animal derived antibodies, "humanized" antibodies often do not undergo an undesirable reaction with the immune system of the subject.

Thus, as used herein, the term "humanized" and its derivatives refers to an antibody which includes any percent above zero and up to 100% of human antibody material, in an amount and composition sufficient to render such an antibody less likely to be immunogenic when administered to a human being. It is being understood that the term "humanized" reads also on human derived antibodies or on antibodies derived from non human cells genetically engineered to include functional parts of the human immune system coding genes, which therefore produce antibodies which are fully human.

The present application discloses characterization of a polyclonal antibody (designated #733) that was raised against 14 amino acid sequence located at the N-terminus of the 50 kDa heparanase enzyme. This antibody reacts specifically with the 50 kDa heparanase form, as evaluated by immunoblotting (FIG. 1A) and immunoprecipitation (FIG. 1B) analyses. Importantly, antibody #733 was able to neutralize the activity of purified active heparanase (FIG. 6A) and to significantly inhibit heparanase activity in live cells (FIG. 6B). This finding suggests that the N-terminal region of the 50 kDa heparanase enzyme participates in the formation of a three-dimensional structure necessary for enzymatic activity, and that antibody #733 binding to this region prevents proper enzyme folding. Alternatively, the neutralizing ability may be due to antibody #733 interference with heparanase interaction with its substrate. Given the specificity of antibody reaction and their therapeutic use in the clinic [Nahta, R. et al., The Oncologist 8, 5-17 (2003)], neutralizing anti-heparanase antibodies are extremely important reagents for basic heparanase research and, possibly, clinical applications. Raising monoclonal antibodies against this 14 amino acid sequence should yield an even better neutralizing ability. Moreover, the #733 antibody was used by the present invention to study heparanase localization and its sub-cellular processing site, two important aspects of heparanase biology [Goldshmidt (2002) ibid.].

Thus, according to a particularly preferred embodiment, the antibody of the invention is an affinity-purified polyclonal antibody designated #733.

In another embodiment, the invention relates to a composition for the inhibition of heparanase glycosidase catalytic activity, comprising as an active ingredient an antibody which specifically recognizes an amino acid sequence derived from the N-terminus region of the 50 Kd subunit of heparanase and is capable of inhibiting heparanase glycosidase catalytic activity, said composition optionally further comprising a pharmaceutically acceptable carrier, diluent, excipient and/or additive.

According to a specifically preferred embodiment, the composition of the invention comprises as an active ingredient the antibody of the invention.

Still further, the invention relates to a pharmaceutical composition for the treatment or the inhibition of a process or a pathologic disorder associated with heparanase catalytic activity. This composition comprises as an active ingredient, an antibody which specifically recognizes an amino acid sequence derived from the N-terminus region of the 50 Kd subunit of heparanase and is capable of inhibiting heparanase glycosidase catalytic activity, in an amount sufficient for the inhibition of heparanase glycosidase catalytic activity. Preferably, the antibody of the invention and most preferably, the affinity purified #733 antibody may be used for the pharmaceutical compositions of the invention. The composition of the invention optionally further comprises a pharmaceutically acceptable carrier, diluent, excipient and/or additive.

According to another specific embodiment, the pharmaceutical composition of the invention is intended for the inhibition and the treatment of a process, such as angiogenesis, tumor formation, tumor progression and tumor metastasis. The composition of the invention may further be used for the treatment of a pathologic disorder associated with heparanase catalytic activity, for example, a malignant proliferative disorder such as a non-solid tumor selected from the group consisting of carcinoma, sarcoma, melanoma, leukemia and lymphoma, an inflammatory disorder, an autoimmune disorder or a kidney disorder.

The invention further provide the use of an antibody which specifically recognizes an amino acid sequence derived from the N-terminus region of the 50 Kd subunit of heparanase and is capable of inhibiting heparanase glycosidase catalytic activity, preferably, the antibody of the invention, and most preferably, the affinity purified antibody #733 of the invention, for the inhibition of heparanase glycosidase catalytic activity.

In another preferred embodiment, the invention relates to the use of an antibody which specifically recognizes an amino acid sequence derived from the N-terminus region of the 50 Kd subunit of heparanase and is capable of inhibiting heparanase glycosidase catalytic activity, preferably, the antibody of the invention, in the preparation of a composition for the inhibition of heparanase glycosidase catalytic activity.

Still further, the invention relates to the use of an antibody which specifically recognizes an amino acid sequence derived from the N-terminus region of the 50 Kd subunit of heparanase and is capable of inhibiting heparanase glycosidase catalytic activity, preferably, the antibody of the invention, in the preparation of a pharmaceutical composition for the treatment or the inhibition of a process or a pathologic disorder associated with heparanase glycosidase catalytic activity. Such composition optionally further comprises a pharmaceutically acceptable carrier, diluent, excipient and/or additive, and is specifically applicable for processes such as angiogenesis, tumor formation, tumor progression and tumor metastasis and for pathologic disorders such as malignant proliferative disorders or inflammatory disorder, autoimmune disorder and a kidney disorder.

The invention further provides a method for the inhibition of heparanase glycosidase catalytic activity comprising the step of in vivo or in vitro contacting heparanase under suitable conditions, with an inhibitory effective amount of an antibody which specifically recognizes an amino acid sequence derived from the N-terminus region of the 50 Kd subunit of heparanase and is capable of inhibiting heparanase glycosidase catalytic activity, or with a composition comprising the same.

According to another embodiment, the invention relates to a method for the inhibition of heparanase glycosidase catalytic activity in a subject in need thereof comprising the step of administering to said subject an inhibitory effective amount of an antibody, preferably the antibody of the invention, which specifically recognizes an amino acid sequence derived from the N-terminus region of the 50 Kd subunit of heparanase and is capable of inhibiting heparanase glycosidase catalytic activity, or of a composition comprising the same.

In yet another embodiment, the invention relates to a method for the inhibition or the treatment of a process or a pathologic disorder associated with heparanase glycosidase catalytic activity comprising the step of administering to a subject in need thereof a therapeutically effective amount of an antibody, preferably, the antibody of the invention, which specifically recognizes an amino acid sequence derived from the N-terminus region of the 50 Kd subunit of heparanase and is capable of inhibiting heparanase glycosidase catalytic activity, or of a composition comprising the same. These methods are specifically applicable for the treatment and the inhibition of a processes such as angiogenesis, tumor formation, tumor progression, tumor metastasis or for the treatment of a pathologic disorders such as malignant proliferative disorders or inflammatory disorder, autoimmune disorder or a kidney disorder, which as indicated herein before, were shown to be associated with heparanase catalytic activity.

The therapeutically 'effective amount' for purposes herein is that determined by such considerations as are known in the art. The amount must be sufficient to inhibit the correct folding of the heparanase molecule and thereby to inhibit heparanase catalytic activity.

Since antibody #733 preferentially recognizes the active form of heparanase, positive staining of archival paraffin sections indicates not only the presence of heparanase, but also its being active. Although most, if not all, human tumors so far examined exhibit heparanase expression, tumor derived cell lines vary considerably in their activity levels [Shteper, P. et al., Oncogene In Press (2003)]. Interestingly, xenografts established from breast MCF7 cells, which exhibit a very low heparanase activity levels in vitro [FIG. 2A, Zcharia (2001) ibid.], were strongly stained with antibody #733 (FIG. 2C*a, b*). This suggests that important regulatory components may have been lost in vitro, yet heparanase up-regulation is regained upon cell growth in vivo. Such regulatory factors are only starting to emerge and may include various hormones such as estrogen [Elkin, M. et al., Can. Res. 63, 8821-8826 (2003)], growth factors and cytokines. Importantly, in MCF7 and PC3 cell xenografts, as well as in a breast tumor biopsy (FIG. 2B-C), heparanase localization resembled the in vitro localization, accumulating perinuclearly in a vesicle-like pattern (FIG. 2B-*b*, C-*b, d*), suggesting that the inventors' in vitro studies reflect heparanase localization in vivo. In other cases, heparanase appeared less localized and more diffusely distributed in the cytoplasm (FIGS. 1C, 2B-*c,d*). This suggests that under different biological settings, heparanase may be localized in different cellular compartments and hence may exert diverse functions.

High activity levels of heparanase found in the urine of diabetic patients [Katz (2002) ibid.] and the more traditional correlation between heparanase activity levels and the metastatic potential of tumor-derived cells [Nakajima (1998) ibid.; Vlodavsky and Friedmann (2001) ibid.], argue for heparanase being a secreted enzyme. In fact, the enzyme is readily released by activated platelets and cells of the immune system [Vlodavsky L., et al., Invasion & Metastasis 12, 112-127 (1992)].

Antibody #733 and any anti-heparanase, preferably, monoclonal antibodies directed to the amino acid sequence of the invention, may provide the basis for a sensitive screening assay able to detect heparanase in body fluids. This will enable a comprehensive study aimed to establish heparanase as a diagnostic marker for human pathologies.

Therefore, in a further embodiment of this aspect, the invention relates to a method for the diagnosis of a process or a pathologic disorder associated with heparanase glycosidase catalytic activity in a mammalian subject. The diagnostic method of the invention comprises the steps of: (a) providing a sample of said subject; (b) contacting said sample with an antibody which specifically recognizes the active form of heparanase; (c) removing any unbound antibody; and (d) detecting the extent of reaction between said antibody and said heparanase active form present in said sample by suitable means.

According to a particular preferred embodiment, the antibody of the invention, and preferably, the #733 antibody, is used for the diagnostic method of the invention.

According to a specific embodiment, the sample used by the diagnostic method of the invention may be as a non-limiting example, body fluids, tissue specimens, tissue extracts, cells, cell extracts and cell lysates. More specifically, the sample used by the diagnostic method of the invention may be a body fluid sample such as blood, lymph, milk, urine, faeces, semen, brain extracts, spinal cord fluid (SCF), appendix, spleen and tonsillar tissue extracts According to another preferred embodiment, a suitable means used by the diagnostic method of the invention for the detection of the active form of heparanase may be a protein based detection assay selected from the group consisting of immunohistochemical staining, Western blot analysis, immunoprecipitation flow cytometry, ELISA and competition assay.

More particularly, as indicated above, the antibodies, including fragments of antibodies, useful in the present invention, may be used to quantitatively and/or qualitatively detect the active form of heparanase in a sample. This can be accomplished by immunofluorescence techniques employing a fluorescently or color-labeled antibody coupled with light microscopic, flow cytometric, or fluorometric detection.

Another specifically preferred embodiment relates to the antibodies of the invention conjugated to a detectable moiety. One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods, which employ a chromogenic substrate for the enzyme. Detection may also be accomplished by visual comparison of the extent of enzymatic reaction of a substrate in comparison with similarly prepared standards.

Detection may be accomplished by using any of a variety of other immunoassays. For example, by radioactive labeling the antibodies of the invention or antibody fragments, it is possible to detect the active form of heparanase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a γ counter or a scintillation counter or by autoradiography.

It is also possible to label an antibody in accordance with the present invention with a fluorescent compound, fluorescence emitting metals, a chemiluminescent compound or a bioluminescent compound.

Still further, the use of such antibody, specific for the active form of heparanase as a research toll is clearly demonstrated by the following Examples. Previously, the inventors have shown that exogenously-added heparanase rapidly interact with primary human fibroblasts, followed by processing of the 65 kDa precursor into an active 50 kDa enzyme [Nadav (2001) ibid.] This uptake and processing pathway was now demonstrated with tumor-derived MDA-435 breast carcinoma and U87 glioma cell cultures (FIG. 3, inset). In fact, heparanase processing was evident in all primary and tumor-derived cell types examined, suggesting that the involved protease(s) is constitutively active and highly abundant. Moreover, processing of exogenously added heparanase has led to the hypothesis that the protease is a membranous enzyme [Nadav (2001) ibid.; Vlodavsky and Friedmann (2001) ibid.]. This experimental system was utilized to determine the localization of the two heparanase forms during uptake and processing of the latent enzyme, using fluorescent immunostaining. As expected, shortly after its application, the 65 kDa heparanase was exclusively localized to the plasma membrane (FIG. 3, second panel, red), presumably interacting with membranous HSPG [Gingis et al, in preparation; Nadav (2001) ibid.].

By 1 hour following application, heparanase staining appeared diffused with minimal processing as evident by a lack of staining with antibody #733 (FIG. 3, third panel). Staining became intense by 3 hours following heparanase application (FIG. 3, fourth and fifth panels, green), a time point at which the 50 kDa heparanase appeared mainly in perinuclear vesicles, identified as lysosomes (FIG. 3, sixth panel). Interestingly, the inventors noted that the 65 kDa heparanase similarly appeared in vesicles that co-localized, at least in part, with the 50 kDa processed form. This suggests that heparanase processing occurs after its internalization and away from the cell membrane. Lysosomal processing was confirmed by the inhibitors chloroquine (FIG. 4A-D) and bafilomycin A1 (FIG. 4E), treatments that completely inhibited heparanase processing in a number of heparanase-transfected cell types (FIG. 4A) and in a reversible manner (FIG. 4B). Moreover, chloroquine also inhibited the processing of membrane-targeted heparanase (FIG. 5D), further arguing for lysosomes, rather than the plasma membrane, as the processing site.

Heparanase biosynthesis has not yet been followed by metabolic labeling. A single 65 kDa band appeared after a short metabolic pulse, corresponding to the 65 kDa pre-proheparanase form (FIG. 1B). Interestingly, this band rapidly disappeared, while a 50 kDa protein was detected instead, starting at 2 hours, and even more so at 4 hours of chase (FIG. 1B). The lag between the pre-proheparanase synthesis and the appearance of the processed 50 kDa form is not entirely clear, but may result from secretion of the 65 kDa latent form, followed by uptake, internalization and processing. If this is indeed the case, the uptake studies of the present invention (FIG. 3) may reflect the in vivo course of heparanase trafficking. Accumulation of the 50 kDa processed form by 4 hours of chase (FIG. 1B) and even more so by 24 hours (data not shown) may suggest that heparanase half-life is at least 24 hours. This stands in contrast with the relatively short half life of HSPG with transmembrane domain, estimated to be 2-3 hours for cultured rat hepatocytes and 5-6 hours for rat ovarian granulosa cells [Egeberg, M. et al, Biochim. Biophy. Acta. 1541, 135-149 (2001)], or even shorter ($T_{1/2}$~25 minutes) for glycosylphosphatidyl-inositol (GPI) anchored HSPG. This suggests that heparanase may normally function in the turnover of lysosomal HSPG, while heparanase secretion may be involved in its pathological aspects.

Therefore, it is to be appreciated that the antibodies of the present invention, which are specifically directed to amino acid residues $Lys^{158}$ to $Asp^{171}$ of heparanase, may be used also as a powerful tool for basic research of different biological and physiological aspects of heparanase and to allow better understanding of the role of heparanase in different biologic processes.

In yet a further aspect, the invention relates to a nucleic acid construct comprising a polynucleotide sequence encoding a heparanase-derived polypeptide, preferably, a human heparanase-derived polypeptide, devoid of all or part of amino acid residues $Lys^{158}$ to $Asp^{171}$, preferably, amino acid residues $Lys^{158}$ to $Asp^{171}$, of heparanase and being devoid of heparanase catalytic activity. The construct of the invention optionally further comprises operably linked regulatory elements.

Preferably, a heparanase-derived polypeptide which devoid all or part of amino acid residues $Lys^{158}$ to $Asp^{171}$, may be encoded by a nucleic acid sequence comprising at least one mutation, point mutation, nonsense mutation, missense mutation, deletion, insertion or rearrangement. In a specifically preferred embodiment, the heparanase-derived polypeptide comprised within the nucleic acid constructs of the invention, may carry a deletion mutation.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded and double-stranded polynucleotides. "Construct", as used herein, encompasses vectors such as plasmids, viruses, bacteriophage, integratable DNA fragments, and other vehicles, which enable the integration of DNA fragments into the genome of the host.

Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. This typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector-containing cells. Plasmids are the most commonly used form of vector but other forms of vectors which serve an equivalent function and which are, or become, known in the art are suitable for use herein. See, e.g., Pouwels et al., Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

According to a specifically preferred embodiment, the polypeptide encoded by the DNA construct of the invention has the amino acid sequence as denoted by SEQ ID NO: 4 and is encoded by a nucleic acid sequence denoted by SEQ ID NO:3.

The invention further provide an expression vector comprising the amino acid construct encoding a mutated heparanase polypeptide, preferably, a human heparanase-derived polypeptide, devoid of all or part of amino acid residues $Lys^{158}$ to $Asp^{171}$ of heparanase and being devoid of heparanase catalytic activity.

Also, a specific embodiment of the invention relates to a host cell transformed or transfected with a construct expressing said mutated 50 Kd subunit of heparanase. Suitable host cells include prokaryotes, lower eukaryotes, and higher eukaryotes. Prokaryotes include gram negative and gram positive organisms, e.g., E. coli and B. subtilis. Lower eukaryotes include yeast, S. cerevisiae and Pichia, and species of the genus Dictyostelium. Higher eukaryotes include established tissue culture cell lines from animal cells, both of non-mammalian origin, e.g., insect cells and birds, and of mammalian origin, e.g., human and other primate, and of rodent origin.

"Host cell" as used herein refers to cells which can be recombinantly transformed with vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

As used herein, the term "transfection" means the introduction of a nucleic acid, e.g., an expression vector, into a recipient cells by nucleic acid-mediated gene transfer.

"Transformation", as used herein, refers to a process in which a cell's genotype is changed as a result of the cellular uptake of exogenous DNA or RNA.

"Cells", "host cells" or "recombinant cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

The invention further provides a mutated recombinant protein comprising heparanase-derived polypeptide devoid of amino acid residues $Lys^{158}$ to $Asp^{171}$ of human heparanase and therefore being devoid of heparanase endoglycosidase catalytic activity.

According to a specifically preferred embodiment, the mutate heparanase molecule of the invention comprises the amino acid sequence substantially as denoted by SEQ ID NO: 4, encoded by the nucleic acid sequence substantially as denoted by SEQ ID NO: 3.

Cell adhesion is a process by which cells associate with each other, migrate towards a specific target or localize within the extra-cellular matrix (ECM). As such, cell adhesion constitutes one of the fundamental mechanisms underlying numerous biological phenomena. For example, cell adhesion is responsible for the adhesion of hematopoietic cells to endothelial cells and the subsequent migration of those hemopoietic cells out of blood vessels and to the site of injury. As such, cell adhesion plays a role in pathologies such as inflammation and immune reactions in mammals.

Results described in a previous application of the present inventors (PCT IL 03/00989) indicate that apart from its well-established role as a HS-degrading enzyme, heparanase may function as a pro-adhesive molecule, independent of its endoglycosidase activity. The combined feature of heparanase as an enzyme and cell adhesion molecule further emphasizes its potential significance in processes involving cell adhesion, migration and invasion, such as tumor metastasis, neo-vascularization, inflammation and autoimmunity.

The unexpected significant adhesive properties of heparanase, revealed previously by the inventors, and particularly the creation of the non-catalytic adhesive heparanase molecule, as disclosed by the present application, enables the inventors to use the recombinant molecules of the invention in promotion and enhancement of adhesion. For example, the use of such novel molecule as a tissue sealant molecule.

Thus, in a further embodiment, the mutated heparanase molecule of the invention may be used as a tissue sealant capable of accelerating, enhancing, stimulating and/or mediating the healing of an injury, homeostasis of an injury to a skin surface or an internal organ, endothelium formation of a blood vessel, adhesive activity of mammalian cells and/or adhesion and aggregation of platelets.

The mutated non-catalytic heparanase molecule of the present invention may further be applicable for a method of treating a mammalian subject suffering from a cell-adhesion mediated pathology. Such method may include administering to said subject a therapeutically effective amount of a substance which inhibits cell-to-cell adhesion or cell-to-matrix adhesion mediated by a non-catalytic membranal heparanase.

More specifically, such cell adhesion mediated pathology may be any one of tumor metastasis, autoimmunity and inflammatory diseases Still further, the invention provides for the use of the mutated heparanase molecule of the invention in the preparation of an agent for promoting the endothelialization of vascular grafts.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Antibodies and Reagents

Antibody #733 was raised against the peptide $^{158}$KKFKN-STYRSSSVD$^{171}$ (also denoted by SEQ ID NO: 1) derived from the N-terminus region of the 50 Kd subunit of heparanase. A cysteine residue was added following Asp171 (also denoted by SEQ ID NO: 2) to enable an efficient coupling of the peptide to kehole limpet hemocyanin (KLH) and to preserve the correct orientation of the peptide. The KLH-conjugated peptide was injected into rabbits and antibody specificity was evaluated by immunoblotting. For affinity purification, the peptide was coupled to agarose beads using Sulfolink kit, according to the manufacturer's instructions (Pierce, Rockford, Ill.).

Antibody #1453 was raised against the entire 65 kDa heparanase precursor isolated from the conditioned medium of heparanase-transfected 293 cells [Zetser, A. et al., Cancer Research (in press) (2003)]. This antibody was affinity purified on immobilized bacterially-expressed 50 kDa heparanase-GST fusion protein [Levy-Adam (2003) ibid.].

Monoclonal anti-heparanase antibody was purchased from Becton-Dickinson (San Diego, Calif.), Cat. No. 612296. This antibody specifically recognizes the latent 65 kDa heparanase precursor.

Monoclonal anti-heparanase antibody 130, recognizing both the 50 kDa and 65 kDa heparanase forms [Vlodavsky (1999a) ibid.], was kindly provided by InSight Ltd (Rehovot, Israel).

Anti-actin and anti cathepsin D monoclonal antibodies were purchased from Sigma (St. Louis, Mo.), Cat. No. C 0715 (anti-Cathepsin D antibody).

Bafilomycin $A_1$ was purchased from Sigma and dissolved in DMSO. Equivalent volume of the vehicle control was always run in parallel.

Plasmid DNA Constructs

The pSecTag 2 vector containing the full-length heparanase cDNA was kindly provided by Dr. Hua-Quan Miao (ImClone Systems Inc, New York, N.Y.) and has been described previously [Levy-Adam (2003) ibid.].

Heparanase-PDGF-R Chimeric Molecule Targeted to the Membrane

For targeting heparanase to the plasma membrane, heparanase cDNA was sub-cloned into the pDisplay vector (Invitrogen, Carlsbad, Calif.) which provides the PDGF-R transmembrane domain as a membrane-anchoring domain. The pcDNA3 plasmid containing the full-length heparanase cDNA was applied as template for heparanase amplification, using the forward 5'-GA-AGA-TCT-CAG-GAC-GTC-GTG-GAC-CTG-3' (denoted as SEQ ID NO: 5) and reversed 5'-CCA-ATG-CAT-TTG-TTC-TGC-AGG-ATG-CAA-GCA-GCA-ACT-TTG-GC-3' (denoted as SEQ ID NO: 6) set of primers. The forward primer contained an inserted BgIII restriction site and the reverse primer contained a PstI restriction site, enabling in frame cloning into the pDisplay multiple cloning site. Following PCR reaction with a proofreading enzyme (pfu, Promega, Madison Wis.), the vector and constructs were digested with BgIII and PstI, and ligated with T4 ligase. DH5α E. Coli strain was used for transformation, and clones resistant to ampicillin were propagated in bacteria and evaluated for the presence of the insert by digestion with BgIII/PstI.

Cloning and Expression of Mutated 50 Kd Subunit of Heparanase, the 50Δ158-172 in Mammalian Cells The pcDNA3 plasmid containing the full length human heparanase cDNA construct was used as the PCR template for generation of the 50Δ158-172 construct. Primers included the following F: 5'-GGA-ATT-CTA-TAC-ACT-TTT-GCA-AAC-TGC-T-3' (also denoted by SEQ ID NO: 7) and R: 5'-GC-CGC-TCG-AGA-GAT-GCA-AGC-AGC-AAC-TTT-GG-3' (also denoted by SEQ ID NO: 8) for amplification of the 50Δ158-172 kDa subunit (Leu$^{173}$-Ile$^{543}$). The forward primer contains an inserted EcoRI restriction site and the reverse primer an Xho restriction site, enabling cloning in frame into the pSecTag2 vector cloning site. Following the PCR with a proofreading enzyme (Pfu-Promega), the vector and the construct were digested with EcoRI and XhoI, and ligated with T4 ligase. DH5α E. Coli strain was used for transformation. Clones resistant to ampicillin were propagated in bacteria and evaluated for the presence of the insert by digestion with EcoRI/XhoI. All PCR amplification products were sequenced to assure correct DNA sequences.

Cell Culture and Transfection

Human U87 glioma, MDA-MB-435 breast carcinoma and Chinese hamster ovary (CHO) cells were purchased from the American Type Culture Collection (ATCC) and were grown in Dulbecco's Modified Eagle's Medium (DMEM) supplemented with 10% FCS and antibiotics.

HEK-293 cells stably transfected with the human heparanase cDNA, were provided by ImClone Systems Ltd. (New York, N.Y.) and rat C6 glioma cells were kindly provided by Dr. Eli Keshet (The Hebrew University School of Medicine, Jerusalem) [Benjamin, L. E. and Keshet, E. Proc. Natl. Acad. Sci. USA 94, 8761-8766 (1997)].

NMU cells were kindly provided by Dr. Marcelle Machluf (Faculty of Biotechnology and Food Engineering, Technion, Haifa).

For stable transfection, sub-confluent MDA-435, C6, NMU and CHO cells were transfected with the pSecTag2 or pDisplay vectors containing the full-length heparanase cDNA, using Fugene reagent according to the manufacturer's (Roche, Mannheim, Germany) instructions. Transfection proceeded for 48 h followed by selection with 400 µg/ml Zeocin (pSecTag2 vector) or 800 µg/ml G418 (pDisplay vector) for two weeks. Stable transfectant pools were further expanded and analyzed.

Immunoblotting, Metabolic Labeling and Immunoprecipitation

Cell extracts were prepared using a lysis buffer containing 50 mM Tris-HCl, pH 7.4, 150 mM NaCl, 0.5% Triton X-100, supplemented with a cocktail of protease inhibitors (Roche, Indianapolis, Ind.). Protein concentration was determined (Bradford reagent, BioRad, Hercules, Calif.) and 30 µg protein was resolved by SDS-PAGE under reducing conditions using 10% gels. After electrophoresis, proteins were transferred to PVDF membrane (BioRad) and probed with the appropriate antibody followed by HRP-conjugated secondary antibody (Jackson ImmunoResearch, West Grove, Pa.) and an enhanced chemiluminescent substrate (Pierce).

Metabolic labeling was performed essentially as described [Ilan, N. et al., Exp. Cell Res. 228, 146-159 (1996)]. Briefly, confluent cell cultures were methionine-starved for 30 minutes prior to the addition of 150 µCi/ml [$^{35}$S]-methionine (Amersham, UK). Cells were pulsed for 20 minutes and chased for the indicated time points in 1 ml of complete growth medium containing excess of cold methionine. For immunoprecipitation, equal volumes (0.1 ml) or equal number of TCA-precipitable cpm of lysate samples were brought to a volume of 1 ml with 50 mM Tris-HCl, pH 7.4, 5 mM EDTA, 150 mM NaCl and 0.5% NP-40 (buffer A) and incubated with the indicated antibody for 2 hours at 4° C. Protein A/G sepharose beads (Santa Cruz) were then added for additional 30 minutes. Beads were collected by centrifugation and washed 3 times with buffer A supplemented with 300 mM NaCl and 5% sucrose and finally with buffer A. Sample buffer was then added and after boiling at 100° C. for 5 minutes, samples were subjected to electrophoresis as described above. Gels were fixed (30 minutes, 25% isopropanol+10% acetic acid) and fluorographed (30 minutes, Amplify, Amersham) before drying and autoradiography.

Heparanase Purification and Uptake Studies

The latent 65 kDa heparanase precursor was purified from the culture medium of heparanase-transfected HEK-293 cells, essentially as described [Zetser (2003) ibid.]. For uptake studies, the 65 kDa heparanase precursor was added to confluent cell cultures at a concentration of 1 µg/ml under serum-free conditions. At the indicated time points, the medium was aspirated, cells were washed twice with ice-cold PBS and total cell lysates were prepared as described. Heparanase uptake and processing were analyzed by immunoblotting with antibody #1453.

Immunohistochemistry

All studies were performed with archival paraffin sections. Slides were de-waxed twice with xylene (5 minutes each) and rehydrated with graded ethanols. Endogenous peroxidase activity was eliminated by incubating the slides for 30 minutes with 1% H$_2$O$_2$ in methanol. Sections were then washed with distilled water and subjected to antigen retrieval by boiling for 5 minutes in a pressure cooker in 20 mM citrate buffer, pH 6. Sections were blocked with 10% normal goat serum in PBS for 60 minutes, followed by over night incubation with primary antibody (diluted in blocking solution) at 4° C. Slides were then extensively washed with PBS containing 0.01% Triton X-100 and incubated with a secondary reagent (Envision kit) according to the manufacturer's instructions (Dako, Glostrup, Denmark). Following additional washes, color was developed with the AEC reagent (Sigma), sections were counterstained with hematoxylin and mounted (Immu-Mount, Shandon, Pittsburgh, Pa.).

Immunocytochemistry

Indirect immunofluorescence staining was performed essentially as described [Zetser (2003) ibid.]. Briefly, cells were grown on glass cover slips and fixed with cold methanol for 10 minutes. Cells were then washed with PBS and subsequently incubated in PBS containing 10% normal goat serum for 1 hour at room temperature, followed by 2 hours incubation with the indicated primary antibodies. Cells were then extensively washed with PBS and incubated with the relevant (Cy2/Cy3-conjugated) secondary antibody (Jackson ImmunoResearch) for 1 hour, washed and mounted (Vectashield, Vector, Burlingame, Calif.).

Flow Cytometry

Cells were detached with trypsin, centrifuged at 1000 RPM for 4 minutes, washed with PBS and counted. Cells ($2\times10^5$) were centrifuged and the pellet was then resuspended in PBS with 1% FCS and incubated with anti c-Myc or anti heparanase monoclonal antibodies for 45 minutes on ice. Cells were then washed twice with PBS and incubated with FITC-conjugated anti mouse IgG for 30 minutes on ice, washed and analyzed using a FACSCalibur fluorescent activated cell sorter and CellQuest software (Becton Dickinson, Mountain View, Calif.).

Heparanase Activity Assay

Preparation of ECM-coated dishes and determination of heparanase activity were performed as described in detail elsewhere [Vlodavsky, I. Current protocols in Cell Biology Vol. 1 pp. 10.14.11-10.14.14, John Wiley & Sons, New York (1999b); Goldshmidt, O. et al., J. Biol. Chem. 276, 29178-29187 (2001); Goldshmidt (2002) ibid.]. Purified active heparanase was kindly provided by Dr H-O. Miao (ImClone Systems Inc., New York, N.Y.). For inhibition studies, twenty ng protein were added to 1 ml serum-free RPMI medium and incubated (1 hour, 4° C.) with 10 µg of rabbit IgG or 10 µg of affinity-purified antibody #733, followed by 1 hour incubation with $^{35}$S-labeled ECM.

For heparanase inhibition studies with live cells, heparanase-transfected 293 cells ($2\times10^5$) were resuspended in RPMI medium and incubated (1 hour, 37° C.) with $^{35}$S-labeled ECM in the presence of 30 µg/ml affinity-purified antibody #733 or control rabbit IgG. The incubation medium containing sulfate labeled degradation fragments was subjected to gel filtration on a Sepharose CL-6B column. Fractions (0.2 ml) were eluted with PBS and their radioactivity counted in a β-scintillation counter. Degradation fragments of HS side chains were eluted at $0.5<K_{av}<0.8$ (peak II, fractions 15-30). Nearly intact HSPGs were eluted just after the Vo ($K_{av}<0.2$, peak I, fractions 3-15).

Example 1

Antibody #733 Raised Against the N-Terminus 14 Amino Acid Sequence of the 50 kd Heparanase Subunit, Preferentially Recognizes the 50 kDa Active Heparanase Form Heparanase is synthesized as a ~65 kDa non-active precursor that is subsequently processed into 8 kDa and 50 kDa subunits that heterodimerize to form an active enzyme [Fairbanks (1999) ibid.; Levy-Adam (2003) ibid.; McKenzie (2003) ibid.].

The inventors have previously characterized an antibody (#810) directed against a peptide located at the C-terminus of the 8 kDa heparanase subunit, that preferentially recognizes the 8 kDa fragment as compared to the 65 kDa heparanase precursor [Levy-Adam (2003) ibid.]. In order to better characterize the cellular distribution of the heparanase subunits, this approach was further utilized and an antibody was raised against a peptide located at the N-terminus of the 50 kDa heparanase subunit. Indeed, as shown by FIG. 1A (733), the antibody that was prepared and designated #733, preferentially recognized the 50 kDa heparanase subunit in immunoblot analysis, but failed to react with the 65 kDa heparanase precursor. In contrast, an antibody that is commercially available (Becton-Dickinson) reacted only with the 65 kDa heparanase precursor (FIG. 1A, BD), while antibody #1453 which was raised against the entire 65 kDa protein, reacted with both the 65 kDa and 50 kDa heparanase forms (FIG. 1A, 1453).

In order to further evaluate the specificity of antibody #733, the inventors next employed metabolic labeling and immunoprecipitation analysis. Heparanase-transfected CHO cells were pulsed for 20 minutes with [$^{35}$S]-methionine and then chased for the indicated time points in complete growth medium supplemented with an excess of cold methionine (FIG. 1B). Immunoprecipitation of lysate samples with mAb 130 which recognizes both the 65 kDa and 50 kDa forms of heparanase [Nadav (2001) ibid.] revealed the synthesis of a single ~65 kDa protein at the end of the pulse period (FIG. 1B, 0). Subsequently, the amount of the 65 kDa heparanase form rapidly declined while a 50 kDa band started to appear after 2 hours (2 h) and accumulated further by 4 hours of chase (4 h, FIG. 2B, upper panel). A similar biosynthesis pattern and kinetics were observed in metabolically labeled heparanase-transfected HEK-293 and U87 glioma cells (not shown). Interestingly, immunoprecipitation of the same lysate samples with antibody #733 failed to detect the 65 kDa heparanase precursor found at time 0, but precipitated the 50 kDa heparanase form found after 2 hours and 4 hours of chase (FIG. 1B, lower panel). Thus, under denatured (immunoblotting) and native (immunoprecipitation) conditions, antibody #733 preferentially recognized the 50 kDa active form of heparanase.

The inventors next evaluated the ability of this antibody to recognize heparanase in paraffin sections subjected to immunohistochemistry. Placenta, which is known to posses high levels of heparanase activity and, moreover, was used as a source for heparanase purification [Goshen, R. et al., Mol. Hum. Reprod. 2, 679-684 (1996); Vlodavsky (1999b) ibid.; Dempsey (2000a) ibid.; Haimov-Kochman, R. et al., Mol. Hu. Rep. 6, 566-573 (2002)] was chosen for immunoprecipitation. As expected, antibody #733 specifically stained the cytotrophoblast cell layer lining the intervillous space (FIG. 1C), in agreement with previously reported placenta staining [Haimov-Kochman (2002) ibid.].

Example 2

Differential Localization of Heparanase Forms and Heparanase Lysosomal Processing as Reveled by the #733 Antibody Having demonstrated the ability of antibody #733 to specifically react with heparanase in immunohistochemistry analysis, xenograft tumor sections derived from prostate PC3 and breast MCF7 cells, two cell lines that exhibit moderate and low heparanase activity profiles in vitro, were stained (FIG. 2A). These xenograft sections were compared with heparanase expression in human prostate and breast tumor biopsies (FIG. 2B-C). Antibody #733 was able to detect heparanase expression in PC3 (FIG. 2B, a-b) and MCF 7 (FIG. 2C, a-b) xenografts, as well as in prostate (FIG. 2B, c-d) and breast (FIG. 2C, c-d) biopsy specimens. Thus, although PC3 and MCF 7 cell lines exhibit relatively low heparanase activity in vitro (FIG. 2A) and undetectable levels of heparanase in immunoblot analysis and immunofluorescence staining (data not shown), heparanase expression appeared to be up-regulated once these tumor-derived cells are introduced back into an animal, and staining intensities are comparable to those observed in human tumor biopsies (FIG. 2B, C, c-d). Interestingly, heparanase was noted to be localized mainly at perinuclear regions rather than diffusely distributed in the cell cytoplasm. This was best demonstrated in PC3 and MCF7 xenografts and breast biopsy staining at a high magnification (FIGS. 2B, b and 2C, b,d), and closely resembled the localization of endogenous [Goldshmidt (2002) ibid.] or exogenously-added [Nadav (2001) ibid.] heparanase.

In order to further study the sub-cellular localization of the two heparanase forms, the processing of exogenous heparanase added to MDA-MB-435 breast cancer and U87 glioma cells, was next examined. For this purpose, the latent 65 kDa heparanase precursor was added at a concentration of 1 μg/ml to confluent MDA-435 and U87 cells and heparanase uptake and processing was evaluated at various time intervals by means of immunoblotting, using the #1453 antibody which recognizes both, the latent (65 Kd) and the active (58 Kd) forms of heparanase. As previously reported for primary fibroblasts, heparanase rapidly reacted with MDA-435 and U87 cells and uptake of the 65 kDa heparanase was detected already 15 minutes following its addition (FIG. 3 inset, 15'). The amount of the 65 kDa heparanase continued to accumulate by 30 and 60 min without detectable processing, which was noted 2 hours after its addition and apparently completed by 4 hours (FIG. 3, inset). Similar uptake and processing kinetics were observed with 293, C6, PC3 and HeLa cell lines (not shown). This uptake and processing pattern enabled the present inventors to study the localization of the two heparanase forms at different time points following its application. To this end, MDA-435 cells were left untreated (FIG. 3, upper panel) or incubated with heparanase (5 μg/ml) for 5 minutes (second panel), 1 hour (third panel) or 3 hours (fourth panel) and double stained with antibodies that distinguish between the latent 65 kDa (BD) and active 50 kDa (#733) forms of heparanase (FIG. 1A). The 65 kDa heparanase precursor was readily detected already 5 minutes after its addition and seemed to be exclusively localized to the plasma membrane (FIG. 3, second panel, left). At 1 hour, the 65 kDa heparanase appeared more diffusely distributed in the cell cytoplasm, with minimal processing detected with antibody #733 staining (FIG. 3, third panel). Abundant heparanase processing was detected by antibody #733 at 3 hours following the addition of heparanase (FIG. 3, fourth panel, middle), in agreement with the immunoblot analysis (FIG. 3, inset), accumulating at perinuclear areas [Nadav (2001) ibid.]. Double immunostaining with antibody #733 and anti-cathepsin D, a lysosomal marker, antibody clearly revealed these perinuclear vesicles as lysosomes (FIG. 3, sixth panel), suggesting that the 50 kDa active heparanase enzyme resides within lysosomal compartments. Interestingly, at this time point the non-processed 65 kDa heparanase precursor also appeared perinuclear, partially co-localizing with the processed form (FIG. 3 fourth panel). Such co-localization of the processed and un-processed heparanase forms was confirmed by additional experiments with human U87 glioma cells, yielding a similar staining pattern (FIG. 3, fifth panel).

Heparanase Processing Requires Active Lysosomes

Heparanase processing site within the cell was not identified to date. Nevertheless, several publications raised the possibility of the plasma membrane as the processing organelle [Nadav (2001) ibid.; Vlodavsky and Friedmann (2001) ibid.]. The appearance of the non-processed 65 kDa heparanase at perinuclear vesicles (FIG. 3 fourth and fifth panels) argues against this hypothesis and suggests that heparanase processing occurs in acidic vesicles, presumably lysosomes. In order to test this hypothesis, HEK-293 (upper panel), MDA-435 (second panel), C6 (third panel) and NMU (fourth panel) cells stably transfected with the human heparanase cDNA were treated with increasing concentrations of chloroquine, an inhibitor of lysosome proteases (FIG. 4A). Chloroquine, which inhibits lysosomal protease activity by raising the lysosome pH, completely inhibited heparanase processing in a dose dependent manner, in all the heparanase-transfected cell lines examined. This effect of chloroquine was reversible and heparanase processing re-appeared upon chloroquine removal (FIG. 4B). Interestingly, treatment of heparanase-transfected NMU cells with chloroquine resulted in the appearance of at least 4 different heparanase species (FIG. 4, fourth panel), suggesting that heparanase processing is more complex then originally thought, involving several steps and possibly different enzymes. Similarly, chloroquine treatment completely inhibited the processing of exogenously-added heparanase (FIG. 4C), resulting in the accumulation of the unprocessed heparanase in large vesicles (FIG. 4D). The necessity of acidified lysosomes for heparanase processing was confirmed by treating cells with bafilomycin A1, a specific inhibitor of vacuolar proton pump [Drose, S. and Altendorf, K. J. Exp. Biol. 200, 1-8 (1997)]. As low as 250 nM bafilomycin A1 completely inhibited heparanase processing in transfected C6 glioma and NMU cells (FIG. 4E), supporting the lysosomes as the heparanase processing organelle. In order to further rule out the plasma membrane as the heparanase processing site, heparanase was targeted to the cell membrane by introducing the PDGF-R transmembrane domain at the heparanase C-terminus. Stably transfected HEK-293 and C6 glioma cells revealed a high expression of this gene construct (FIG. 5A) and membrane localization was verified by FACS analysis (FIG. 5B) and immunofluorescence staining (FIG. 5C). The protein product of this hybrid gene construct was processed into the expected 50 kDa heparanase form (FIG. 5A). This stands in contrast to the heparanase-GFP hybrid which failed to be processed [Goldshmidt, O. et al., Exp. Cell Res. 281, 50-61 (2002)], suggesting that the introduced transmembrane domain does not interfere with heparanase processing. Processing of the membrane-bound heparanase may be brought about by a membranous protease, or can take place in lysosomes as part of membrane recycling. If the latter possibility is correct, processing of the membrane-bound heparanase should also be inhibited by chloroquine. Indeed, incubation of HEK-293 and rat C6 glioma cells expressing the membrane-targeted heparanase with chloroquine completely abolished heparanase processing (FIG. 5D), suggesting that the protease(s) responsible for heparanase processing resides within the lysosome and requires acidic pH.

Example 3

Antibody #733, Specific for the N-Terminus Region of the 50 Kd Subunit of Heparanase, Inhibits Heparanase Enzymatic Activity The preferential recognition by antibody #733 of the processed 50 kDa heparanase as compared to the non-processed 65 kDa form (FIG. 1A) suggests that the N-terminus of the 50 kDa protein undergoes conformational changes upon heparanase processing, exposing an epitope that is not present in the 65 kDa heparanase precursor. Although this region is not considered to be part of the heparanase active site [Hulett, M. D. et al., Biochemistry 39, 15659-15667 (2000)], it may well be involved in a three-dimensional organization assumed by the 50 kDa heparanase upon processing, and that is necessary for enzymatic activity. To test this hypothesis, purified heparanase was incubated with affinity-purified antibody #733 or control rabbit IgG, and enzymatic activity was determined. As shown in FIG. 6A, antibody #733 significantly inhibited heparanase enzymatic activity. Moreover, antibody #733 also inhibited heparanase activity in live 293 cells (FIG. 6B). Raising monoclonal antibodies directed against this peptide may result in a better inhibitory antibody and provide a specific molecular tool to study heparanase function under normal and pathological conditions.

Example 4

A Synthetic Peptide Comprising Amino Acid Residues 158 to 171 of Heparanase Completely Blocks Heparanase Catalytic Activity As indicated above, the use of an antibody (#733) which specifically binds the 14-15 amino acid sequence derived from the N-terminus region of the heparanase 50 Kd subunit, indicated that this sequence may be involved in a three-dimensional organization necessary for heparanase enzymatic activity.

To further investigate the importance of this sequence in heparanase catalytic activity, competition experiments were next performed. In these experiments, recombinant active heparanase (40 ng) was incubated (2 h, pH 7) with different concentrations of a peptide containing the amino acid sequence of residues 158 to 171, or with a control scrambled peptide (Scr), and enzymatic activity was determined. As shown in FIG. 7, a peptide containing the amino acid sequence of residues 158 to 171, significantly inhibited heparanase enzymatic activity, in a dose dependent manner. Thus, excess of a peptide containing such sequence may compete with the endogenous corresponding sequence within the heparanase molecule which may interact with a particular domain to form appropriate three-dimensional conformation of the active molecule and thereby interrupt the organization required for proper catalytic activity of heparanase. These results further support the hypothesis that the 158-171 sequence is required for a proper folding of the active molecule.

Example 5

A Mutated Heparanase Molecule Having a Deletion of the 158 to 172 Amino Acid Sequence is Devoid of Heparanase Catalytic Activity Still further, in order to disturb correct folding of heparanase molecule, the inventors next constructed a construct encoding the 50 kDa subunit of heparanase in which amino acids 158-172 were deleted, as described in Experimental procedures. Cells (293 cells) were transfected with the 8 kDa and the wild type 50 kDa heparanase subunit or the mutated 50 kDa subunit in which amino acids 158-172 were deleted, and heparanase activity was evaluate compared with control, mock transfected cells. As clearly shown by FIG. 8, complete inhibition of heparanase activity was demonstrated upon deletion of the N-terminal, 158-172, sequence.

What is claimed is:

1. An isolated peptide, consisting of the sequence from amino acid residue $Lys^{158}$ to amino acid residue $Asp^{171}$ of the N-terminus region of the 50 Kd subunit of human heparanase, wherein said sequence is required for heparanase catalytic activity and deletion of said sequence from the N-terminus of the 50 Kd subunit of heparanase results in an inactive heparanase molecule.

2. An isolated and purified peptide selected from the group consisting of:
   a) a peptide consisting of the amino acid sequence of residues $Lys^{158}$ to $Asp^{171}$ of the N-terminus region of the 50 Kd subunit of human heparanase, said peptide inhibiting heparanase catalytic activity;
   b) a peptide of a) having an insertion of one to two amino acid residues, said peptide inhibiting heparanase catalytic activity,
   c) a peptide of a) having deletions of one to two amino acid residues, wherein said peptide comprises residues 158-162 of human heparanase and inhibits heparanase catalytic activity,
   d) a peptide of a) extended at the N-terminus or C-terminus or at both termini by one or two amino acids, said peptide inhibiting heparanase catalytic activity; and
   e) a dimer or multimer of a) or d), said peptide inhibiting heparanase catalytic activity.

3. The peptide according to claim 2, wherein said peptide has at least one of a N terminal cysteine and a C terminal cysteine.

4. An isolated and purified peptide, selected from the group consisting of amino acid sequences as set forth by SEQ ID NO: 1 and SEQ ID NO: 2.

5. The peptide according to claim 4, wherein said peptide is set forth by SEQ ID NO: 1.

6. The peptide according to claim 4, wherein said peptide is set forth by SEQ ID NO: 2.

7. A composition for the inhibition of heparanase glycosidase catalytic activity comprising, as an active ingredient, an isolated and purified peptide selected from the group consisting of:
   a) a peptide consisting of the amino acid sequence of residues $Lys^{158}$ to $Asp^{171}$ of the N-terminus region of the 50 Kd subunit of human heparanase, said peptide inhibiting heparanase catalytic activity;
   b) a peptide of a) having an insertion of one to two amino acid residues, said peptide inhibiting heparanase catalytic activity,
   c) a peptide of a) having deletions of one to two amino acid residues, wherein said peptide comprises residues 158-162 of human heparanase and inhibits heparanase catalytic activity,
   d) a peptide of a) extended at the N-terminus or C-terminus or at both termini by one or two amino acids, said peptide inhibiting heparanase catalytic activity; and
   e) a dimer or multimer of a) or d), said peptide inhibiting heparanase catalytic activity.

8. The composition according to claim 7, wherein said peptide has at least one of a N terminal cysteine and a C terminal cysteine.

9. The composition according to claim 7, further comprising an additive.

10. The composition according to claim 9, wherein said additive is selected from the group consisting of a pharmaceutically acceptable carrier, diluent, and excipient.

11. A composition for the inhibition of heparanase glycosidase catalytic activity comprising, as an active ingredient, an isolated and purified peptide selected from the group consisting of amino acid sequences set forth by SEQ ID NO: 1 and SEQ ID NO: 2, said composition further comprising a pharmaceutically-acceptable carrier, diluent, excipient, or additive.

12. The composition according to claim 11, wherein said peptide is set forth by SEQ ID NO: 1.

13. The composition according to claim 11, wherein said peptide is set forth by SEQ ID NO: 2.

14. A composition comprising, as an active ingredient, an isolated and purified peptide as set forth by SEQ ID NO:1, and a pharmaceutically acceptable carrier, wherein said carrier is selected from the group consisting of a diluent, an excipient, and an additive.

15. A composition comprising, as an active ingredient, an isolated and purified peptide as set forth by SEQ ID NO:2, and a pharmaceutically acceptable carrier, wherein said carrier is selected from the group consisting of a diluent, an excipient, and an additive.

16. A pharmaceutical composition for treating a pathologic disorder comprising, as an active ingredient, an isolated and purified peptide selected from the group consisting of:
   a) a peptide consisting of the amino acid sequence of residues $Lys^{158}$ to $Asp^{171}$ of the N-terminus region of the 50 Kd subunit of human heparanase, said peptide inhibiting heparanase catalytic activity;
   b) a peptide of a) having an insertion of one to two amino acid residues, said peptide inhibiting heparanase catalytic activity, c) a peptide of a) having deletions of one to two amino acid residues, wherein said peptide comprises residues 158-162 of human heparanase and inhibits heparanase catalytic activity, d) a peptide of a) extended at the N-terminus or C-terminus or at both termini by one or two amino acids, said peptide inhibiting heparanase catalytic activity; and e) a dimer or multimer of a) or d), said peptide inhibiting heparanase catalytic activity, wherein said pathologic disorder is any one of an inflammatory disorder, kidney disorder, autoimmune disorder, and a malignant proliferative disorder selected from the group consisting of carcinoma, sarcoma, melanoma, leukemia, and lymphoma.

17. The composition according to claim 16, wherein said peptide has at least one of a N terminal cysteine and a C terminal cysteine.

18. The pharmaceutical composition according to claim 16, further comprising an additive.

19. The pharmaceutical composition according to claim 18, wherein said additive is selected from the group consisting of a pharmaceutically acceptable carrier, diluent, and excipient.

20. A pharmaceutical composition for treating a pathologic disorder comprising, as an active ingredient, an isolated and purified peptide selected from the group consisting of SEQ ID NO: 1 and SEQ ID NO: 2, wherein said pathologic disorder is any one of an inflammatory disorder, kidney disorder, autoimmune disorder, and a malignant proliferative disorder selected from the group consisting of carcinoma, sarcoma, melanoma, leukemia, and lymphoma.

21. The pharmaceutical composition according to claim 20, wherein said peptide is set forth by SEQ ID NO: 1.

22. The pharmaceutical composition according to claim 20, wherein said peptide is set forth by SEQ ID NO: 2.

23. A method for using an isolated and purified peptide in the preparation of a composition for inhibiting heparanase glycosidase catalytic activity, which method comprises:

(i) providing an isolated and purified peptide, wherein said peptide is selected from the group consisting of:
  a) a peptide consisting of the amino acid sequence of residues $Lys^{158}$ to $Asp^{171}$ of the N-terminus region of the 50 Kd subunit of human heparanase, said peptide inhibiting heparanase catalytic activity;
  b) a peptide of a) having an insertion of one to two amino acid residues, said peptide inhibiting heparanase catalytic activity,
  c) a peptide of a) having deletions of one to two amino acid residues, wherein said peptide comprises residues 158-162 of human heparanase and inhibits heparanase catalytic activity,
  d) a peptide of a) extended at the N-terminus or C-terminus or at both termini by one or two amino acids, said peptide inhibiting heparanase catalytic activity; and
  e) a dimer or multimer of a) or d), said peptide inhibiting heparanase catalytic activity; and (ii) admixing said peptide with a carrier, diluent, excipient, or additive.

24. The method according to claim 23, wherein said peptide is set forth by SEQ ID NO:1.

25. The method according to claim 23, wherein said peptide is set forth by SEQ ID NO:2.

26. A method of using an isolated and purified peptide to prepare a pharmaceutical composition for the treatment of a pathological disorder, which method comprises:

i) providing an isolated and purified peptide, wherein said peptide is selected from the group consisting of:
  a) a peptide consisting of the amino acid sequence of residues $Lys^{158}$ to $Asp^{171}$ of the N-terminus region of the 50 Kd subunit of human heparanase, said peptide inhibiting heparanase catalytic activity;
  b) a peptide of a) having an insertion of one to two amino acid residues, said peptide inhibiting heparanase catalytic activity,
  c) a peptide of a) having deletions of one to two amino acid residues, wherein said peptide comprises residues 158-162 of human heparanase and inhibits heparanase catalytic activity,
  d) a peptide of a) extended at the N-terminus or C-terminus or at both termini by one or two amino acids, said peptide inhibiting heparanase catalytic activity; and
  e) a dimer or multimer of a) or d), said peptide inhibiting heparanase catalytic activity, and (ii) admixing said peptide with a pharmaceutically-acceptable carrier, diluent, excipient, or additive, wherein said pathologic disorder is any one of an inflammatory disorder, kidney disorder, autoimmune disorder, and a malignant proliferative disorder selected from the group consisting of carcinoma, sarcoma, melanoma, leukemia, and lymphoma.

27. The method according to claim 26, wherein said peptide is set forth by SEQ ID NO:1.

28. The method according to claim 26, wherein said peptide is set forth by SEQ ID NO:2.

29. A method for inhibition of heparanase glycosidase catalytic activity comprising:

in vivo or in vitro contacting heparanase under suitable conditions, with an inhibitory effective amount of an isolated and purified peptide or composition including said peptide, wherein said peptide is selected from the group consisting of:
  a) a peptide consisting of the amino acid sequence of residues $Lys^{158}$ to $Asp^{171}$ of the N-terminus region of the 50 Kd subunit of human heparanase, said peptide inhibiting heparanase catalytic activity;
  b) a peptide of a) having an insertion of one to two amino acid residues, said peptide inhibiting heparanase catalytic activity,
  c) a peptide of a) having deletions of one to two amino acid residues, wherein said peptide comprises residues 158-162 of human heparanase and inhibits heparanase catalytic activity,
  d) a peptide of a) extended at the N-terminus or C-terminus or at both termini by one or two amino acids, said peptide inhibiting heparanase catalytic activity; and
  e) a dimer or multimer of a) or d), said peptide inhibiting heparanase catalytic activity.

30. The method according to claim 29, wherein said peptide is set forth by SEQ ID NO:1.

31. The method according to claim 29, wherein said peptide is set forth by SEQ ID NO:2.

32. A method for inhibition of heparanase glycosidase catalytic activity in a subject in need thereof, comprising:

administering to said subject an inhibitory effective amount of an isolated and purified peptide or a composition including said peptide, wherein said peptide is selected from the group consisting of:
  a) a peptide consisting of the amino acid sequence of residues $Lys^{158}$ to $Asp^{171}$ of the N-terminus region of the 50 Kd subunit of human heparanase, said peptide inhibiting heparanase catalytic activity;

b) a peptide of a) having an insertion of one to two amino acid residues, said peptide inhibiting heparanase catalytic activity, c) a peptide of a) having deletions of one to two amino acid residues, wherein said peptide comprises residues 158-162 of human heparanase and inhibits heparanase catalytic activity, d) a peptide of a) extended at the N-terminus or C-terminus or at both termini by one or two amino acids, said peptide inhibiting heparanase catalytic activity; and e) a dimer or multimer of a) or d), said peptide inhibiting heparanase catalytic activity.

33. The method according to claim 32, wherein said peptide is set forth by SEQ ID NO:1.

34. The method according to claim 32, wherein said peptide is set forth by SEQ ID NO:2.

35. A method for treatment of a pathologic disorder wherein said pathologic disorder is any one of an inflammatory disorder, kidney disorder, autoimmune disorder, and a malignant proliferative disorder selected from the group consisting of carcinoma, sarcoma, melanoma, leukemia, and lymphoma, said method comprising:

administering to a subject in need thereof a therapeutically effective amount of an isolated and purified peptide or of a composition including said peptide, wherein said peptide is selected from the group consisting of:

a) a peptide consisting of the amino acid sequence of residues $Lys^{158}$ to $Asp^{171}$ of the N-terminus region of the 50 Kd subunit of human heparanase, said peptide inhibiting heparanase catalytic activity;

b) a peptide of a) having an insertion of one to two amino acid residues, said peptide inhibiting heparanase catalytic activity, c) a peptide of a) having deletions of one to two amino acid residues, wherein said peptide comprises residues 158-162 of human heparanase and inhibits heparanase catalytic activity, d) a peptide of a) extended at the N-terminus or C-terminus or at both termini by one or two amino acids, said peptide inhibiting heparanase catalytic activity; and e) a dimer or multimer of a) or d), said peptide inhibiting heparanase catalytic activity.

36. The method according to claim 35, wherein said peptide is set forth by SEQ ID NO:1.

37. The method according to claim 35, wherein said peptide is set forth by SEQ ID NO:2.

* * * * *

SEQUENCE LISTING

<160> NUMBER OF SEQ ID NOS: 8

<210> SEQ ID NO 1
<211> LENGTH: 14
<212> TYPE: PRT
<213> ORGANISM: Homo sapiens

<400> SEQUENCE: 1

Lys Lys Phe Lys Asn Ser Thr Tyr Ser Arg Ser Ser Val Asp
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Residues 158 to 171 of human heparanase with an
      additional cysteine residue

<400> SEQUENCE: 2

Lys Lys Phe Lys Asn Ser Thr Tyr Ser Arg Ser Ser Val Asp Cys
1               5                   10                  15

<210> SEQ ID NO 3
<211> LENGTH: 1765
<212> TYPE: DNA
<213> ORGANISM: Homo sapiens

<400> SEQUENCE: 3
ccagcgctgc tccccgggcg ctcctccccg ggcgctcctc cccaggcctc ccgggcgctt      60
ggatcccggc catctccgca cccttcaagt gggtgtgggt gatttcctgg cgggggagc     120 agccaggtga gcccaagatg ctgctgcgct cgaagcctgc gctgccgccg ccgctgatgc     180
tgctgctcct ggggccgctg gtcccctct ccctggcgc cctgccccga cctgcgcaag      240
cacaggacgt cgtggacctg gacttcttca cccaggagcc gctgcacctg gtgagcccct     300
cgttcctgtc cgtcaccatt gacgccaacc tggccacgga cccgcggttc ctcatcctcc     360
tgggttctcc aaagcttcgt accttggcca gaggcttgtc tcctgcgtac ctgaggtttg     420
gtggcaccaa gacagacttc ctaattttcg atcccaagaa ggaatcaacc tttgaagaga     480
gaagttactg gcaatctcaa gtcaaccagg atatttgcaa atatggatcc atccctcctg     540
atgtggagga agttacggt tggaatggc cctaccagga gcaattgcta ctccgagaac      600
actaccagct atacactttt gcaaactgct caggactgga cttgatcttt ggcctaaatg     660
cgttattaag aacagcagat ttgcagtgga acagttctaa tgctcagttg ctcctggact     720
actgctcttc caaggggtat aacatttctt gggaactagg caatgaacct aacagtttcc     780
ttaagaaggc tgatatttc atcaatgggt cgcagttagg agaagatttt attcaattgc      840
ataaacttct aagaaagtcc accttcaaaa atgcaaaact ctatggtcct gatgttggtc     900
agcctcgaag aaagacggct aagatgctga agcttcct gaaggctggt ggagaagtga      960
ttgattcagt tacatggcat cactactatt tgaatggacg gactgctacc agggaagatt    1020
ttctaaaccc tgatgtattg gacatttta tttcatctgt gcaaaaagtt tccaggtgg      1080 ttgagagcac caggcctggc aagaaggtct ggttaggaga acaagctct gcatatgag      1140 gcggagcgcc cttgctatcc gacacctttg cagctggctt tatgtggctg ataaattgg     1200 gcctgtcagc ccgaatggga atagaagtgg tgatgaggca agtattcttt ggagcaggaa    1260

```
actaccattt agtggatgaa aacttcgatc ctttacctga ttattggcta tctcttctgt    1320
tcaagaaatt ggtgggcacc aaggtgttaa tggcaagcgt gcaaggttca aagagaagga    1380
agcttcgagt ataccttcat tgcacaaaca ctgacaatcc aaggtataaa gaaggagatt    1440
taactctgta tgccataaac ctccataatg tcaccaagta cttgcggtta ccctatcctt    1500
tttctaacaa gcaagtggat aaataccttc taagaccttt gggacctcat ggattacttt    1560
ccaaatctgt ccaactcaat ggtctaactc taaagatggt ggatgatcaa accttgccac    1620
ctttaatgga aaaacctctc cggccaggaa gttcactggg cttgccagct ttctcatata    1680 gttttttgt gataagaaat gccaaagttg ctgcttgcat ctgaaaataa aatatactag    1740
tcctgacaaa aaaaaaaaaa aaaaa                                          1765
```

<210> SEQ ID NO 4
<211> LENGTH: 528
<212> TYPE: PRT
<213> ORGANISM: Homo sapiens

<400> SEQUENCE: 4

```
Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
                20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
    130                 135                 140

Pro Tyr Gln Glu Gln Leu Leu Leu Arg Glu His Tyr Gln Leu Tyr Thr
145                 150                 155                 160

Phe Ala Asn Cys Ser Gly Leu Asp Leu Ile Phe Gly Leu Asn Ala Leu
                165                 170                 175

Leu Arg Thr Ala Asp Leu Gln Trp Asn Ser Ser Asn Ala Gln Leu Leu
            180                 185                 190

Leu Asp Tyr Cys Ser Ser Lys Gly Tyr Asn Ile Ser Trp Glu Leu Gly
        195                 200                 205

Asn Glu Pro Asn Ser Phe Leu Lys Lys Ala Asp Ile Phe Ile Asn Gly
    210                 215                 220

Ser Gln Leu Gly Glu Asp Phe Ile Gln Leu His Lys Leu Leu Arg Lys
225                 230                 235                 240

Ser Thr Phe Lys Asn Ala Lys Leu Tyr Gly Pro Asp Val Gly Gln Pro
                245                 250                 255

Arg Arg Lys Thr Ala Lys Met Leu Lys Ser Phe Leu Lys Ala Gly Gly
            260                 265                 270

Glu Val Ile Asp Ser Val Thr Trp His His Tyr Tyr Leu Asn Gly Arg
        275                 280                 285
```

```
Thr Ala Thr Arg Glu Asp Phe Leu Asn Pro Asp Val Leu Asp Ile Phe
    290                 295                 300

Ile Ser Ser Val Gln Lys Val Phe Gln Val Val Glu Ser Thr Arg Pro
305                 310                 315                 320

Gly Lys Lys Val Trp Leu Gly Glu Thr Ser Ala Tyr Gly Gly Gly
                325                 330                 335

Ala Pro Leu Leu Ser Asp Thr Phe Ala Ala Gly Phe Met Trp Leu Asp
                340                 345                 350

Lys Leu Gly Leu Ser Ala Arg Met Gly Ile Glu Val Val Met Arg Gln
                355                 360                 365

Val Phe Phe Gly Ala Gly Asn Tyr His Leu Val Asp Glu Asn Phe Asp
    370                 375                 380

Pro Leu Pro Asp Tyr Trp Leu Ser Leu Leu Phe Lys Lys Leu Val Gly
385                 390                 395                 400

Thr Lys Val Leu Met Ala Ser Val Gln Gly Ser Lys Arg Arg Lys Leu
                405                 410                 415

Arg Val Tyr Leu His Cys Thr Asn Thr Asp Asn Pro Arg Tyr Lys Glu
                420                 425                 430

Gly Asp Leu Thr Leu Tyr Ala Ile Asn Leu His Asn Val Thr Lys Tyr
                435                 440                 445

Leu Arg Leu Pro Tyr Pro Phe Ser Asn Lys Gln Val Asp Lys Tyr Leu
    450                 455                 460

Leu Arg Pro Leu Gly Pro His Gly Leu Leu Ser Lys Ser Val Gln Leu
465                 470                 475                 480

Asn Gly Leu Thr Leu Lys Met Val Asp Asp Gln Thr Leu Pro Pro Leu
                485                 490                 495

Met Glu Lys Pro Leu Arg Pro Gly Ser Ser Leu Gly Leu Pro Ala Phe
                500                 505                 510

Ser Tyr Ser Phe Phe Val Ile Arg Asn Ala Lys Val Ala Ala Cys Ile
                515                 520                 525

<210> SEQ ID NO 5
<211> LENGTH: 26
<212> TYPE: DNA
<213> ORGANISM: Artificial Sequence
<220> FEATURE:
<223> OTHER INFORMATION: Sequence of a primer

<400> SEQUENCE: 5
gaagatctca ggacgtcgtg gacctg                                  26

<210> SEQ ID NO 6
<211> LENGTH: 41
<212> TYPE: DNA
<213> ORGANISM: Artificial Sequence
<220> FEATURE:
<223> OTHER INFORMATION: Sequence of a primer

<400> SEQUENCE: 6
ccaatgcatt tgttctgcag gatgcaagca gcaactttgg c                 41

<210> SEQ ID NO 7
<211> LENGTH: 27
<212> TYPE: DNA
<213> ORGANISM: Artificial Sequence
<220> FEATURE:
<223> OTHER INFORMATION: Sequence of a primer

<400> SEQUENCE: 7
```

```
ggaattctat acacttttgc aaactgc                                    27
```

<210> SEQ ID NO 8
<211> LENGTH: 29
<212> TYPE: DNA
<213> ORGANISM: Artificial Sequence
<220> FEATURE:
<223> OTHER INFORMATION: Sequence of a primer

<400> SEQUENCE: 8

```
gccgctcgag agatgcaagc agcaacttt                                  29
```